United States Patent
Gill et al.

(10) Patent No.: US 8,989,852 B2
(45) Date of Patent: Mar. 24, 2015

(54) SYSTEMS AND METHODS FOR USE BY IMPLANTABLE MEDICAL DEVICES FOR DETECTING AND DISCRIMINATING STROKE AND CARDIAC ISCHEMIA USING ELECTROCARDIAC SIGNALS

(75) Inventors: Jong Gill, Valencia, CA (US); Rupinder Bharmi, Canyon Country, CA (US); Edward Karst, South Pasadena, CA (US); Ryan Rooke, Redondo Beach, CA (US); Riddhi Shah, Mountain View, CA (US); Fujian Qu, Sunnyvale, CA (US); Gene A. Bornzin, Simi Valley, CA (US); Taraneh G. Farazi, San Jose, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 506 days.

(21) Appl. No.: 13/207,307

(22) Filed: Aug. 10, 2011

(65) Prior Publication Data

US 2013/0041274 A1 Feb. 14, 2013

(51) Int. Cl.
| | |
|---|---|
| *A61B 5/0452* | (2006.01) |
| *A61B 5/0468* | (2006.01) |
| *A61B 5/00* | (2006.01) |
| *A61B 5/0205* | (2006.01) |
| *A61B 5/0215* | (2006.01) |
| *A61B 5/042* | (2006.01) |
| *A61N 1/37* | (2006.01) |

(Continued)

(52) U.S. Cl.
CPC ............ *A61B 5/0468* (2013.01); *A61B 5/0031* (2013.01); *A61B 5/0205* (2013.01); *A61B 5/02158* (2013.01); *A61B 5/0422* (2013.01); *A61B 5/4839* (2013.01); *A61N 1/3702* (2013.01); *A61B 5/02405* (2013.01); *A61B 5/0295* (2013.01)
USPC ........................................................ 600/513

(58) Field of Classification Search
USPC ........................................................ 600/513
See application file for complete search history.

(56) References Cited

U.S. PATENT DOCUMENTS

| | | | |
|---|---|---|---|
| 4,485,813 A | 12/1984 | Anderson et al. | 600/488 |
| 4,535,774 A | 8/1985 | Olson | 607/24 |

(Continued)

OTHER PUBLICATIONS

Burch et al. "A New Electrocardiographic Pattern Observed in Cerebrovascular Accidents" Circulation 9:720, 1954.

(Continued)

*Primary Examiner* — Luther Behringer

(57) ABSTRACT

Techniques are provided for detecting and distinguishing stroke and cardiac ischemia based on electrocardiac signals. In one example, the device senses atrial and ventricular signals within the patient along a set of unipolar sensing vectors and identifies certain morphological features within the signals such as PR intervals, ST intervals, QT intervals, T-waves, etc. The device detects changes, if any, within the morphological features such as significant shifts in ST interval elevation or an inversion in T-wave shape, which are indicative of stroke or cardiac ischemia. By selectively comparing changes detected along different unipolar sensing vectors, the device distinguishes or discriminates stroke from cardiac ischemia within the patient. The discrimination may be corroborated using various physiological and hemodynamic parameters. In some examples, the device further identifies the location of the ischemia within the heart. In still other examples, the device detects cardiac ischemia occurring during stroke.

15 Claims, 12 Drawing Sheets

(51) Int. Cl.
*A61B 5/024* (2006.01)
*A61B 5/0295* (2006.01)

(56) References Cited

U.S. PATENT DOCUMENTS

| | | | |
|---|---|---|---|
| 4,719,921 A | 1/1988 | Chirife | 607/23 |
| 4,733,667 A | 3/1988 | Olive et al. | 607/24 |
| 4,759,366 A | 7/1988 | Callaghan | 607/26 |
| 4,884,576 A | 12/1989 | Alt | 607/18 |
| 5,113,869 A | 5/1992 | Nappholz et al. | 600/508 |
| 5,135,004 A | 8/1992 | Adams et al. | 600/508 |
| 5,193,550 A * | 3/1993 | Duffin | 600/510 |
| 5,199,428 A | 4/1993 | Obel et al. | 607/44 |
| 5,203,326 A | 4/1993 | Collins | 607/4 |
| 5,313,953 A | 5/1994 | Yomtov et al. | 600/508 |
| 5,328,460 A | 7/1994 | Lord et al. | 604/67 |
| 5,531,768 A * | 7/1996 | Alferness | 607/6 |
| 5,800,467 A | 9/1998 | Park et al. | 607/17 |
| 6,016,443 A | 1/2000 | Ekwall et al. | 600/519 |
| 6,021,350 A | 2/2000 | Mathson | 607/17 |
| 6,044,299 A | 3/2000 | Nilsson | 607/19 |
| 6,050,952 A | 4/2000 | Hakki et al. | 600/485 |
| 6,108,577 A | 8/2000 | Benser | 600/517 |
| 6,112,116 A | 8/2000 | Fischell et al. | 600/517 |
| 6,115,628 A | 9/2000 | Stadler et al. | 600/517 |
| 6,128,526 A | 10/2000 | Stadler et al. | 600/517 |
| 6,208,900 B1 | 3/2001 | Ecker et al. | 607/17 |
| 6,233,486 B1 | 5/2001 | Ekwall et al. | 607/17 |
| 6,256,538 B1 | 7/2001 | Ekwall | 607/17 |
| 6,264,606 B1 | 7/2001 | Ekwall et al. | 600/300 |
| 6,272,379 B1 | 8/2001 | Fischell et al. | 607/5 |
| 6,381,493 B1 | 4/2002 | Stadler et al. | 607/9 |
| 6,468,263 B1 * | 10/2002 | Fischell et al. | 604/890.1 |
| 6,473,647 B1 | 10/2002 | Bradley | 607/27 |
| 6,501,983 B1 | 12/2002 | Natarajan et al. | 607/517 |
| 6,512,952 B2 | 1/2003 | Stahmann et al. | 607/9 |
| 6,609,023 B1 | 8/2003 | Fischell et al. | 600/515 |
| 6,628,988 B2 | 9/2003 | Kramer et al. | 607/9 |
| 6,643,546 B2 | 11/2003 | Mathis et al. | 607/9 |
| 6,711,439 B1 | 3/2004 | Bradley et al. | 607/9 |
| 6,788,970 B1 | 9/2004 | Park et al. | 607/17 |
| 6,937,896 B1 | 8/2005 | Kroll | 607/9 |
| 6,961,615 B2 | 11/2005 | Kroll et al. | 607/18 |
| 6,985,771 B2 | 1/2006 | Fischell et al. | 607/3 |
| 7,099,718 B1 | 8/2006 | Thacker et al. | 607/117 |
| 7,107,096 B2 | 9/2006 | Fischell et al. | 600/515 |
| 7,139,609 B1 | 11/2006 | Min et al. | 607/17 |
| 7,207,947 B2 | 4/2007 | Koh et al. | 600/529 |
| 7,218,960 B1 | 5/2007 | Min et al. | 600/509 |
| 7,225,015 B1 | 5/2007 | Min et al. | 600/517 |
| 7,235,530 B2 | 6/2007 | Blair et al. | 514/12 |
| 7,245,968 B1 | 7/2007 | Farazi et al. | 706/25 |
| 7,272,436 B2 | 9/2007 | Gill et al. | 600/513 |
| 7,297,114 B2 | 11/2007 | Gill et al. | 600/365 |
| 7,400,920 B1 | 7/2008 | Gill et al. | 600/516 |
| 7,460,900 B1 | 12/2008 | Gill et al. | 600/509 |
| 7,502,644 B2 | 3/2009 | Gill et al. | 600/516 |
| 7,524,287 B2 | 4/2009 | Bharmi | 600/365 |
| 7,529,580 B2 | 5/2009 | Gill et al. | 600/513 |
| 7,577,478 B1 | 8/2009 | Kroll et al. | 607/9 |
| 7,599,733 B1 | 10/2009 | Wirasinghe et al. | 600/510 |
| 7,610,086 B1 | 10/2009 | Ke et al. | 600/517 |
| 7,620,448 B1 | 11/2009 | Farazi et al. | 600/515 |
| 7,643,872 B2 | 1/2010 | Min et al. | 600/517 |
| 7,648,464 B1 | 1/2010 | Gill et al. | 600/508 |
| 7,653,436 B2 | 1/2010 | Schecter | 607/17 |
| 7,654,964 B1 | 2/2010 | Kroll et al. | 600/486 |
| 7,697,978 B1 | 4/2010 | Farazi | 600/515 |
| 7,738,956 B1 | 6/2010 | Farazi et al. | 607/9 |
| 7,756,571 B1 | 7/2010 | Farazi | 600/517 |
| 7,756,572 B1 | 7/2010 | Fard et al. | 600/517 |
| 7,769,436 B1 | 8/2010 | Boileau et al. | 600/509 |
| 7,792,572 B1 | 9/2010 | Gill et al. | 600/509 |
| 7,813,805 B1 | 10/2010 | Farazi | 607/50 |
| 7,844,333 B1 | 11/2010 | Koh et al. | 607/17 |
| 7,856,268 B2 | 12/2010 | Kroll et al. | 607/14 |
| 7,869,869 B1 | 1/2011 | Farazi | 607/7 |
| 2004/0059220 A1 | 3/2004 | Mourad et al. | 600/442 |
| 2006/0167365 A1 | 7/2006 | Bharmi | 600/517 |
| 2006/0167517 A1 | 7/2006 | Gill et al. | 607/25 |
| 2006/0167518 A1 | 7/2006 | Gill et al. | 607/25 |
| 2006/0167519 A1 | 7/2006 | Gill et al. | 607/25 |
| 2007/0016031 A1 | 1/2007 | Mourad et al. | 600/437 |
| 2007/0156056 A1 | 7/2007 | Min et al. | 600/509 |
| 2009/0177103 A1 | 7/2009 | Bharmi | 600/516 |
| 2009/0177104 A1 | 7/2009 | Gill et al. | 600/517 |
| 2009/0177105 A1 | 7/2009 | Gill et al. | 600/517 |
| 2009/0318822 A1 | 12/2009 | Qu et al. | 600/515 |
| 2009/0318987 A1 | 12/2009 | Kroll et al. | 607/4 |
| 2010/0081952 A1 | 4/2010 | Gill et al. | 600/515 |
| 2010/0198082 A1 | 8/2010 | Park | 600/483 |
| 2010/0234906 A1 | 9/2010 | Koh | 607/3 |
| 2011/0004111 A1 | 1/2011 | Gill et al. | 600/510 |

OTHER PUBLICATIONS

Venkatesan, "Rare skills in medicine : Diagnosing stroke with the help of Electrocardiogram", Feb. 11, 2010, http://drsvenkatesan.wordpress.com/2010/02/11/rare-skills-in-medicine-diagnosing-stroke-with-the-help-of-electrocardiogram/.

* cited by examiner

SYSTEMS AND METHODS FOR USE BY IMPLANTABLE MEDICAL DEVICES FOR DETECTING AND DISCRIMINATING STROKE AND CARDIAC ISCHEMIA USING ELECTROCARDIAC SIGNALS

FIELD OF THE INVENTION

The invention generally relates to implantable medical devices such as pacemakers, implantable cardioverter/defibrillators (ICDs), cardiac resynchronization therapy devices (CRTs) and, in particular, to techniques for detecting and distinguishing stroke and cardiac ischemia within patients in which such devices are implanted.

BACKGROUND OF THE INVENTION

A stroke is a sudden loss of brain function caused by a blockage of a blood vessel to the brain (ischemic stroke) or a rupture of a blood vessel to the brain (hemorrhagic stroke). It is particularly desirable to detect stroke using an implantable medical device as many elderly patients prone to stroke already have such devices implanted therein or are candidates for such devices. Techniques for detecting stroke for use with implantable medical devices are described in published U.S. Patent Application No. 2010/0198082 of Park, entitled "Systems and Methods for use with an Implantable Medical Device for Detecting Stroke Based on Electrocardiac Signals" and in U.S. patent application Ser. No. 12/558,385 of Bharmi et al., filed Sep. 11, 2009, entitled "System and Method for use with an Implantable Medical Device for Detecting Stroke based on Physiological and Electrocardiac Indices."

Cardiac ischemia is a condition whereby heart tissue does not receive adequate amounts of oxygen and is usually caused by a blockage of an artery leading to heart tissue. If sufficiently severe, cardiac ischemia results in an acute myocardial infarction (AMI), also referred to as a heart attack. With AMI, a substantial portion of heart muscle ceases to function because it no longer receives oxygen, usually due to significant blockage of the coronary artery. However, many episodes of cardiac ischemia are not sufficiently serious to cause actual permanent injury to the heart tissue. Nevertheless, it is desirable to detect such instances of "silent" cardiac ischemia. Note that cardiac ischemia is distinct from an ischemic stroke. Cardiac ischemia is an ischemia occurring within the heart that affects heart function. Ischemic stroke is an ischemia occurring within the brain that affects brain function.

Various techniques have been developed for analyzing morphological features of intracardiac electrogram (IEGM) signals sensed by implantable medical devices in an effort to detect cardiac ischemia. Some IEGM-based ischemia detection techniques seek to detect ischemia by identifying changes in the elevation of the ST interval of the IEGM that occur during cardiac ischemia. The ST interval represents the portion of the cardiac signal between ventricular depolarization (also referred to as an R-wave or QRS complex) and ventricular repolarization (also referred to as a T-wave). The elevation of the ST interval can increase or decrease due to cardiac ischemia or other factors.

Techniques for detecting cardiac ischemia using ST intervals or other features of the IEGM are discussed, for example, in U.S. Pat. No. 6,108,577 to Benser, entitled "Method and Apparatus for Detecting Changes in Electrocardiogram Signals" and U.S. patent application Ser. No. 11/394,724, of Ke et al., filed Mar. 31, 2006, entitled "Ischemia Detection using T-wave Amplitude, QTmax and ST Segment Elevation and Pattern Classification Techniques" and U.S. Pat. No. 7,225,015, entitled "System and Method for Detecting Cardiac Ischemia Based on T-Waves Using an Implantable Medical Device" to Min et al. See, also, U.S. Pat. No. 7,756,572 to Fard et al., entitled "System and Method for Efficiently Distinguishing among Cardiac Ischemia, Hypoglycemia and Hyperglycemia using an Implantable Medical Device and an External System."

See, also, the following U.S. Patents assigned to Pacesetter, Inc., which discuss ischemia: U.S. Pat. No. 7,856,268, entitled "Ischemia Detection for Anti-Arrhythmia Therapy"; U.S. Pat. No. 7,792,572, entitled "Ischemia Detection using Intra-Cardiac Signals"; U.S. Pat. No. 7,756,572, entitled "System and Method for Efficiently Distinguishing Among Cardiac Ischemia, Hypoglycemia and Hyperglycemia using an Implantable Medical Device and an External System"; U.S. Pat. No. 7,648,464, entitled "Detecting Ischemia using an Implantable Cardiac Device based on Morphology of Cardiac Pressure Signal"; U.S. Pat. No. 7,610,086, entitled "System and Method for Detecting Cardiac Ischemia in Real-Time using a Pattern Classifier Implemented within an Implanted Medical Device"; U.S. Pat. No. 7,577,478, entitled "Ischemia Detection for Anti-Arrhythmia Therapy"; U.S. Pat. No. 7,502,644, entitled "System and Method for Distinguishing among Cardiac Ischemia, Hypoglycemia and Hyperglycemia using an Implantable Medical Device"; U.S. Pat. No. 7,460,900, entitled "Method and Apparatus for Detecting Ischemia using Changes in QRS Morphology"; U.S. Pat. No. 7,297,114, entitled "System and Method for Distinguishing among Cardiac Ischemia, Hypoglycemia and Hyperglycemia using an Implantable Medical Device"; U.S. Pat. No. 7,272,436, also entitled "System and Method for Distinguishing among Cardiac Ischemia, Hypoglycemia and Hyperglycemia using an Implantable Medical Device"; U.S. Pat. No. 7,769,436, entitled "System and Method for Adaptively Adjusting Cardiac Ischemia Detection Thresholds and other Detection Thresholds used by an Implantable Medical Device"; U.S. Pat. No. 7,524,287, entitled "System and Method for Distinguishing between Hypoglycemia and Hyperglycemia using an Implantable Medical Device"; U.S. Pat. No. 7,643,872, entitled "System and Method for Detecting Cardiac Ischemia based on T-Waves using an Implantable Medical Device"; U.S. Pat. No. 7,225,015, also entitled "System and Method for Detecting Cardiac Ischemia based on T-waves using an Implantable Medical Device"; U.S. Pat. No. 7,218,960, also entitled "System and Method for Detecting Cardiac Ischemia based on T-waves using an Implantable Medical Device" and U.S. Pat. No. 7,844,333, entitled "Pacing Therapy for Transient Ischemia Treatment."

See, also, the following published U.S. Patent Applications: U.S. Patent Application 2011/0004111, entitled "Ischemia Detection Using Intra-Cardiac Signals;" U.S. Patent Application 2010/0081952, entitled "Detecting Ischemia Using An Implantable Cardiac Device Based On Morphology Of Cardiac Pressure Signal"; Patent Application 2009/0318987, entitled "Ischemia Detection For Anti-Arrhythmia Therapy"; Patent Application No. 2009/0177105, 2009/0177104, 2009/0177103, 2006/0167519, 2006/0167518, 2006/0167517 and 2006/0167365, each entitled "System and Method for Distinguishing Among Cardiac Ischemia, Hypoglycemia And Hyperglycemia using an Implantable Medical Device." See, also, published U.S. Patent Applications: 2007/0016031 and 2004/0059220, both entitled "Systems and Methods for making Noninvasive Assessments of Cardiac Tissue and Parameters" and U.S. Patent Application 2007/0156056, entitled "System and Method for Detecting Cardiac Ischemia based on T-Waves using an Implantable Medical Device."

Still further, see U.S. Pat. No. 5,113,869 to Nappholz; U.S. Pat. No. 5,135,004 to Adams et al.; U.S. Pat. No. 5,199,428 to Obel et al.; U.S. Pat. No. 5,203,326 to Collins; U.S. Pat. No. 5,313,953 to Yomtov et al; U.S. Pat. No. 6,501,983 to Natarajan, et al.; U.S. Pat. Nos. 6,016,443, 6,233,486, 6,256,538, and 6,264,606 to Ekwall; U.S. Pat. No. 6,021,350 to Mathson; U.S. Pat. Nos. 6,128,526, 6,115,628 and 6,381,493 to Stadler et al.; and U.S. Pat. Nos. 7,107,096, 6,985,771, 6,609,023, 6,468,263, 6,272,379, and 6,112,116, each to Fischell et al.

Hence, a variety of morphological features of electrocardiac signals can be used to detect cardiac ischemia. (Herein, electrocardiac signals generally pertain to cardiac electrical signals observed using any of a variety of sensing or detection techniques, including IEGM signals, surface electrocardiogram (EKG) signals or other suitable and appropriate signals, such as impedance signals.) Some of these parameters can also be affected by stroke. In this regard, disruptions in blood supply to the brain caused by stroke may lead to alterations of cardiac autonomic tone, such as increased sympathetic nerve activity. Thus stroke may lead to neurally mediated changes in electrophysiological properties of the heart that differ from those due to cardiac ischemia.

Accordingly, it is desirable to provide techniques for distinguishing stroke from cardiac ischemia. One such technique based on an analysis of electrocardiac signals and hemodynamic parameters is described in U.S. patent application Ser. No. 12/722,206 of Park, filed Mar. 11, 2010, entitled "Systems and Methods for use by an Implantable Medical Device for Detecting and Discriminating Stroke and Cardiac Ischemia using Electrocardiac Signals and Hemodynamic Parameters." Briefly, techniques are described therein where a preliminary indication of stroke is detected based on an analysis of certain features of the IEGM, such as the onset of prominent U-waves, the onset of notched T-waves, and changes in ST segment duration or QT duration. Upon detection of a possible stroke, the device then detects one or more hemodynamic parameters that are typically affected by cardiac ischemia, such as cardiac contractility or stroke volume. The device then distinguishes stroke and cardiac ischemia from one another based on whether any changes detected in the hemodynamic parameters are consistent with cardiac ischemia.

It would be desirable to develop additional or alternative techniques for distinguishing stroke from cardiac ischemia and it is to these ends that the invention is generally directed.

SUMMARY

In an exemplary embodiment, a method is provided for use with an implantable medical device for implant within a patient for distinguishing stroke from cardiac ischemia. The device senses atrial and ventricular electrocardiac signals within the patient along a plurality of sensing vectors and detects morphological features within the signals, such as PR intervals, ST intervals, QT intervals, T-waves, etc. The device detects changes in the morphological features associated with stroke and/or cardiac ischemia, such as a shift in ST interval elevation or an inversion in T-wave shape. The device determines whether the changes in the morphological features are relatively global or relatively local and then distinguishes stroke from cardiac ischemia within the patient, if occurring, based on whether the changes are global or local.

The determination of whether the changes in the morphological features are relatively global or relatively local can be made, for example, by determining whether changes are observed both within IEGMs derived from atrial unipolar signals and within IEGMs derived from ventricular unipolar signals. If both the atrial and ventricular IEGMs exhibit significant changes in the morphological features, the changes are global changes, which are likely due to stroke. If significant changes are observed only in the morphological features of the atrial IEGM or the ventricular IEGM but not both, then the changes are local changes, which are likely due to a cardiac ischemia. Based on this determination, the device can then take action such as by delivering therapy appropriate to either stroke or cardiac ischemia, issuing warning signals to the patient or clinician specifying the detected condition and/ or recording suitable diagnostic information. The rate of change (if any) in the features of the IEGM can also be used to distinguish stroke from cardiac ischemia since such changes are typically faster in response to stroke than cardiac ischemia. Also, in some examples, bipolar sensing vectors can be exploited, particularly to assess local changes in morphological parameters.

In an illustrative example wherein unipolar signals are exploited, the device is equipped to sense signals along a set of unipolar sensing vectors including a right atrial (RA) tip— can vector, a left ventricle (LV) tip—can vector and a right ventricle (RV) tip—can vector, where the "can" is the device housing or casing, which is used as the return electrode. The RA and RV leads are implanted within the RA chamber and the RV chamber, respectively. The LV lead may be positioned on the surface of the LV chamber via the coronary sinus (CS.) The device selects at least one atrial unipolar sensing vector and at least one ventricular unipolar sensing vector and then senses atrial and ventricular IEGM signals within the heart of the patient using those vectors. Selected morphological features are detected within the atrial and ventricular IEGMs and monitored to detect changes that might be indicative of a possible stroke or cardiac ischemia. For the atrial IEGM, a significant change in the PR interval elevation can be indicative of stroke or cardiac ischemia, where the PR interval refers to the portion of the atrial IEGM between a near-field P-wave and a far-field R-wave. For the ventricular IEGM, a significant change in the ST interval elevation can be indicative of stroke or cardiac ischemia, where the ST interval refers to the portion of the ventricular IEGM between the near-field QRS-complex and the subsequent near-field T-wave.

Other morphological features of the ventricular IEGM that can be monitored include the shape of the T-wave and the length of QT intervals. An inversion in the shape of the T-wave may be indicative of stroke or cardiac ischemia. An elongation of the QT interval may also be indicative of stroke or cardiac ischemia. If significant changes are observed in the features of the atrial IEGM (e.g., significant changes the PR interval elevation) and also in the features of the ventricular IEGM (e.g., significant changes ST interval elevation, QT interval duration and the shape of the T-wave), then the changes are deemed to be global and are attributed to stroke, which is systemic and can affect both the atria and ventricles. If significant changes are observed only in the features of the ventricular IEGM but not in the features of the atrial IEGM, then the changes are attributed to a ventricular cardiac ischemia. If significant changes are observed only in the features of the atrial IEGM but not in the features of the ventricular IEGM, then the changes are attributed to an atrial cardiac ischemia. Although only a single atrial IEGM and a single ventricular IEGM can potentially be used, the device can advantageously exploit a greater number of unipolar sensing vectors. For example, multiple vectors can be exploited within the ventricles to further specify the location of a ventricular ischemia.

Various physiological parameters, hemodynamic parameters or cardiac rhythm parameters detected by the device can be used to confirm or corroborate the determination of whether the condition is stroke or cardiac ischemia. For example, the heart rate can be monitored. An increase in heart rate is typically associated with stroke but not cardiac ischemia. As another example, heart rate variability (HRV) can be monitored. Reductions in HRV may be more pronounced from stroke than when cardiac ischemia occurs. Other parameters that can be monitored include signals representative of one or more of: blood volume; blood pressure; pre-ejection interval; heart rate turbulence (HRT), evoked response; capture threshold; kidney function; heart rate alternans, stroke volume and contractility. For example, a sudden increase in blood pressure may be due to cardiac ischemia and hence would tend to corroborate a diagnosis of ischemia. Pre-ejection intervals tend to become longer during cardiac ischemia but become shorter during stroke. Capture thresholds tend to increase due to cardiac ischemia, at least in the vicinity of the ischemia. Alternans tends to occur in conjunction with cardiac ischemia but not stroke. A variety of these parameters can be evaluated and then combined to yield a "score," which is then used to corroborate the determination of stroke vs. cardiac ischemia.

If cardiac ischemia is indicated, it is desirable to identify the location of the ischemia. To this end, the magnitude of changes to the morphological features of a set of atrial and ventricular signals can be assessed and compared. It is believed that these parameters will change by a greater amount in the vicinity of the ischemia. Hence, if the device is equipped to detect electrocardiac signals along multiple vectors within the atrial and ventricular chambers, the signals can be compared to determine which signals exhibited the largest magnitude variations in the morphological parameters, which is thereby indicative of the location of the ischemia. In particular, if a quad-pole LV lead is employed, the device may be able to identify the particular location within the LV of an LV ischemia, which might be helpful in coordinating CRT.

In some cases, cardiac ischemia can occur during stroke. To detect cardiac ischemia during stroke, the magnitude of changes to the morphological features of the atrial and ventricular signals is also assessed and compared. It is believed that these parameters will change by a greater amount if cardiac ischemia occurs during stroke than in response to stroke only, at least in the vicinity of the ischemia. Hence, in circumstances where stroke is indicated because the morphological changes within the IEGM signals appear to be global, it is desirable to additionally assess and compare the magnitude of changes to detect a possible cardiac ischemia contemporaneous with the stroke. Appropriate therapy can then be delivered and suitable warnings generated.

BRIEF DESCRIPTION OF THE DRAWINGS

The above and further features, advantages and benefits of the invention will be apparent upon consideration of the descriptions herein taken in conjunction with the accompanying drawings, in which:

FIGS. 3-1 and 3-2 illustrate an exemplary embodiment of the general technique of FIG. 2, wherein the device discriminates stroke and cardiac ischemia based on the atrial and ventricular unipolar electrocardiac signals and the corroborates the determination using other parameters such as heart rate and HRV;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Unipolar IEGM-based Stroke/Ischemia Discrimination System

Figure 1:
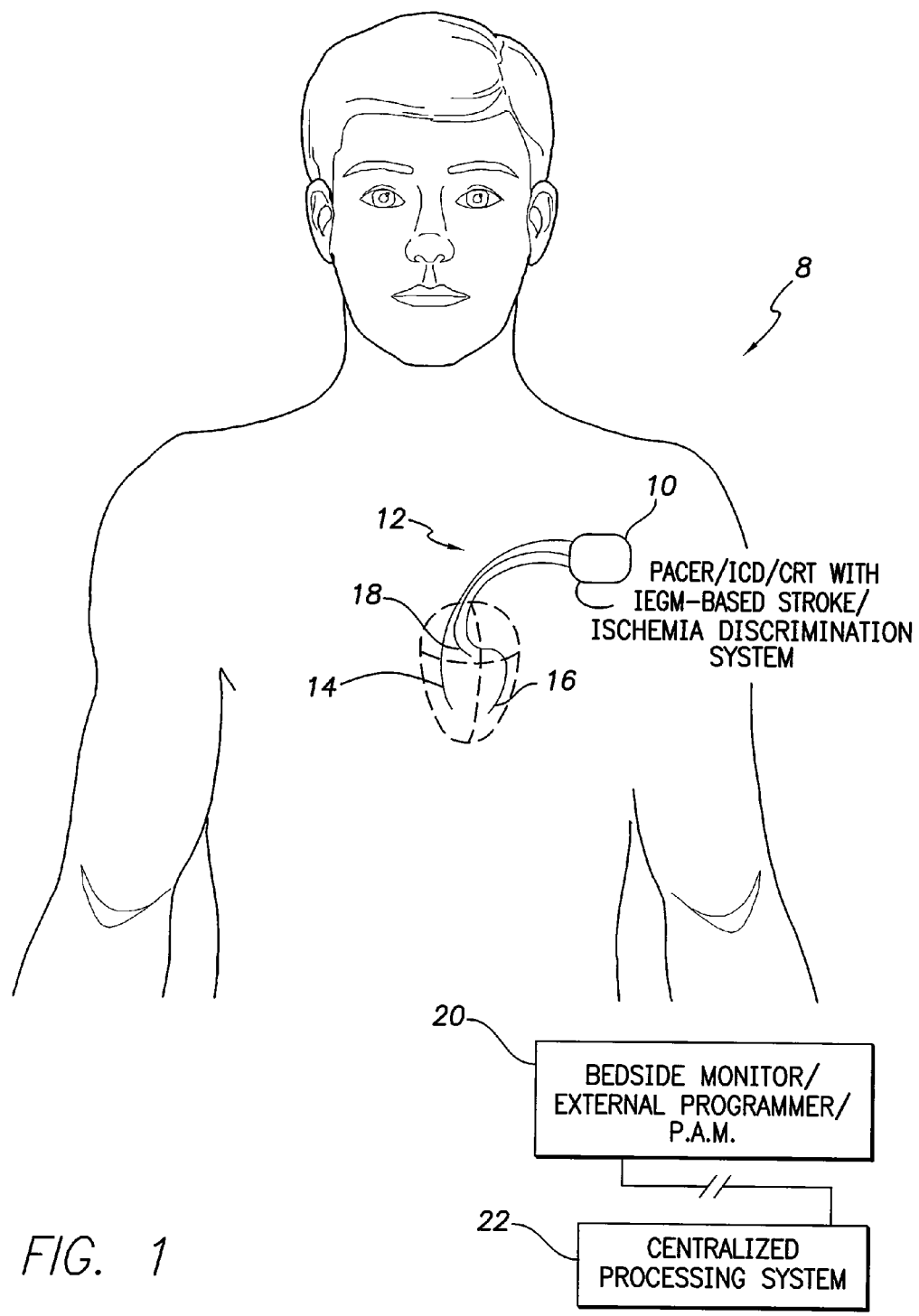
FIG. 1 illustrates pertinent components of a pacer/ICD/CRT equipped with an IEGM-based stroke/ischemia discrimination system capable of detecting and distinguishing stroke and cardiac ischemia.
Figure 10:
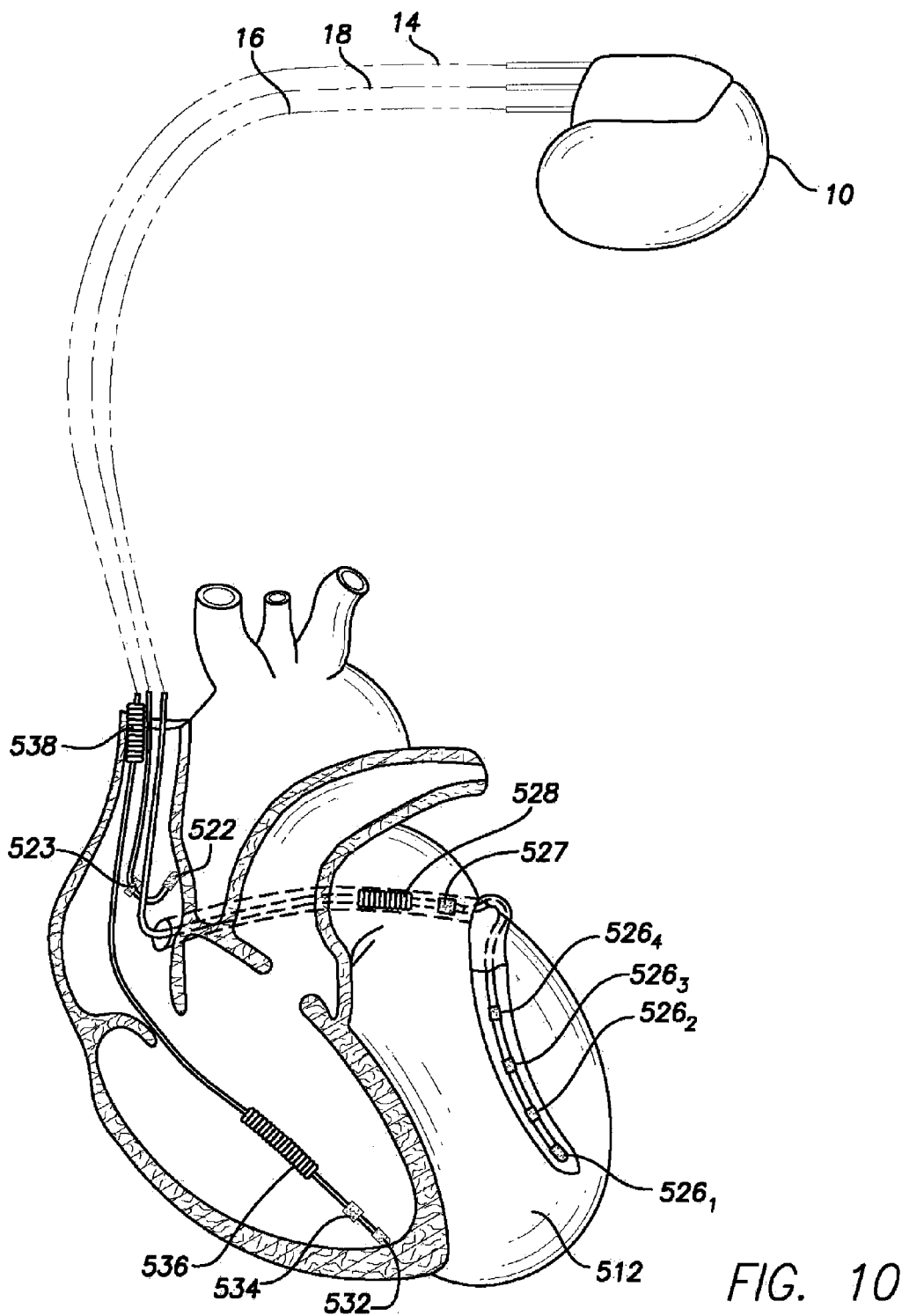
FIG. 10 is a simplified, partly cutaway view of the heart of a patient, illustrating the exemplary pacer/ICD of FIG. 1, along with a set of leads implanted in the heart of the patient.

FIG. 1 illustrates an implantable medical system 8 having a pacemaker, ICD or CRT 10 equipped with an IEGM-based stroke/ischemia discrimination system for detecting and distinguishing stroke and cardiac ischemia within the patient in which the system is implanted based on various electrocardiac signals sensed via a set of leads 12. In this example, three leads are provided: an RV lead 14, an LV/CS lead 16 and an RA lead 18 from which various atrial and ventricular IEGM signals are obtained. The leads are shown in FIG. 1 in stylized form. A more complete and accurate representation of the leads is illustrated in FIG. 10, described below. Although not shown in FIG. 1, one or more hemodynamic or physiological sensors may be mounted to the leads for use in detecting various hemodynamic or physiological parameters to corroborate the detection of stroke or cardiac ischemia. In some cases, the sensors will be components of the pacemaker, ICD or CRT itself.

Upon detection and discrimination of stroke or cardiac ischemia, warning signals may be transmitted to a bedside monitor, external programmer or personal advisory module (PAM) 20 or other external system to alert family members or caregivers of the condition. The external system can also forward warning signals or other suitable information via a centralized processing system 22 to the patient's primary care physician or, in the case of stroke, to emergency personnel. The centralized system may include such systems as the HouseCall™ remote monitoring system or the Merlin@home/Merlin.Net systems of St. Jude Medical. Warnings pertinent to stroke/cardiac ischemia may also be generated using an internal warning device provided within the pacer/ICD. The internal warning device can be a vibrating device or a "tickle" voltage device that, in either case, provides perceptible stimulation to the patient to alert the patient. In addition, diagnostic information pertaining to the stroke/cardiac ischemia may be stored within the pacer/ICD for subsequent transmission to an external programmer for review by a clinician during a follow-up session between patient and clinician. The clinician then prescribes appropriate therapies including medication regimes. The clinician may also adjust the operation of the implanted device to activate, deactivate or otherwise control any therapies automatically provided by the device.

Also, in response to the detection of stroke or cardiac ischemia, therapy can be delivered to the patient by the implantable system. For example, the implantable system can be equipped with a subcutaneous drug pump (not shown in FIG. 1) or other implantable drug dispensation device capable of the delivering medications directly to patient tissues. Implantable drug pumps for use in dispensing medications are discussed in U.S. Pat. No. 5,328,460 to Lord, et al., entitled "Implantable Medication Infusion Pump Including Self-Contained Acoustic Fault Detection Apparatus." (This patent also discusses implantable "tickle" warning devices that may be used to deliver warning signals.)

Additionally, the pacemaker, ICD or CRT may perform a wide variety of pacing and/or defibrillation functions, such as delivering routine pacing, generating and delivering shocks in response to ventricular fibrillation (VF) and delivering CRT. Briefly, CRT seeks to normalize asynchronous cardiac electrical activation and resultant asynchronous contractions associated with congestive heart failure (CHF) by delivering synchronized pacing stimulus to both ventricles. The stimulus is synchronized so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis et al., entitled "Multi-Electrode Apparatus and Method for Treatment of Congestive Heart Failure"; U.S. Pat. No. 6,628,988 to Kramer et al., entitled "Apparatus and Method for Reversal of Myocardial Remodeling with Electrical Stimulation"; and U.S. Pat. No. 6,512,952 to Stahmann et al., entitled "Method and Apparatus for Maintaining Synchronized Pacing". See, also, U.S. Pat. No. 7,653,436 to Schecter, entitled "Global Cardiac Performance."

Thus, FIG. 1 provides an overview of the systems of the invention. Embodiments may be implemented that do not necessarily perform all of the described functions. For example, embodiments may be implemented that provide, for example, for detecting and distinguishing stroke and cardiac ischemia and generating warnings but which do not automatically deliver therapy in response to the stroke or cardiac ischemia. Drug pumps are not necessarily implanted. Bedside monitors or PAMs are not necessarily used. Some implementations may employ some form of external device for generating warning signals but no internal warning device. Other embodiments might include additional implanted devices or components, such as neurostimulators for selectively stimulating portions of the brain or nervous system. These are just a few exemplary embodiments. No attempt is made herein to describe all possible combinations of components that may be provided in accordance with the general principles of the invention. For brevity, implantable medical device 10 will be referred to herein as a "pacer/ICD" but it should be understood that it can additionally or alternatively provide CRT functions and hence may comprise a CRT-P or a CRT-D device or other cardiac rhythm management device.

Note also that the particular shapes, sizes and locations of the implanted components shown in FIG. 1 are merely illustrative and may not necessarily correspond to actual implant locations. Implant locations for the leads are more precisely illustrated in FIG. 10.

Overview of IEGM-based Stroke/Ischemia Discrimination

Figure 2:
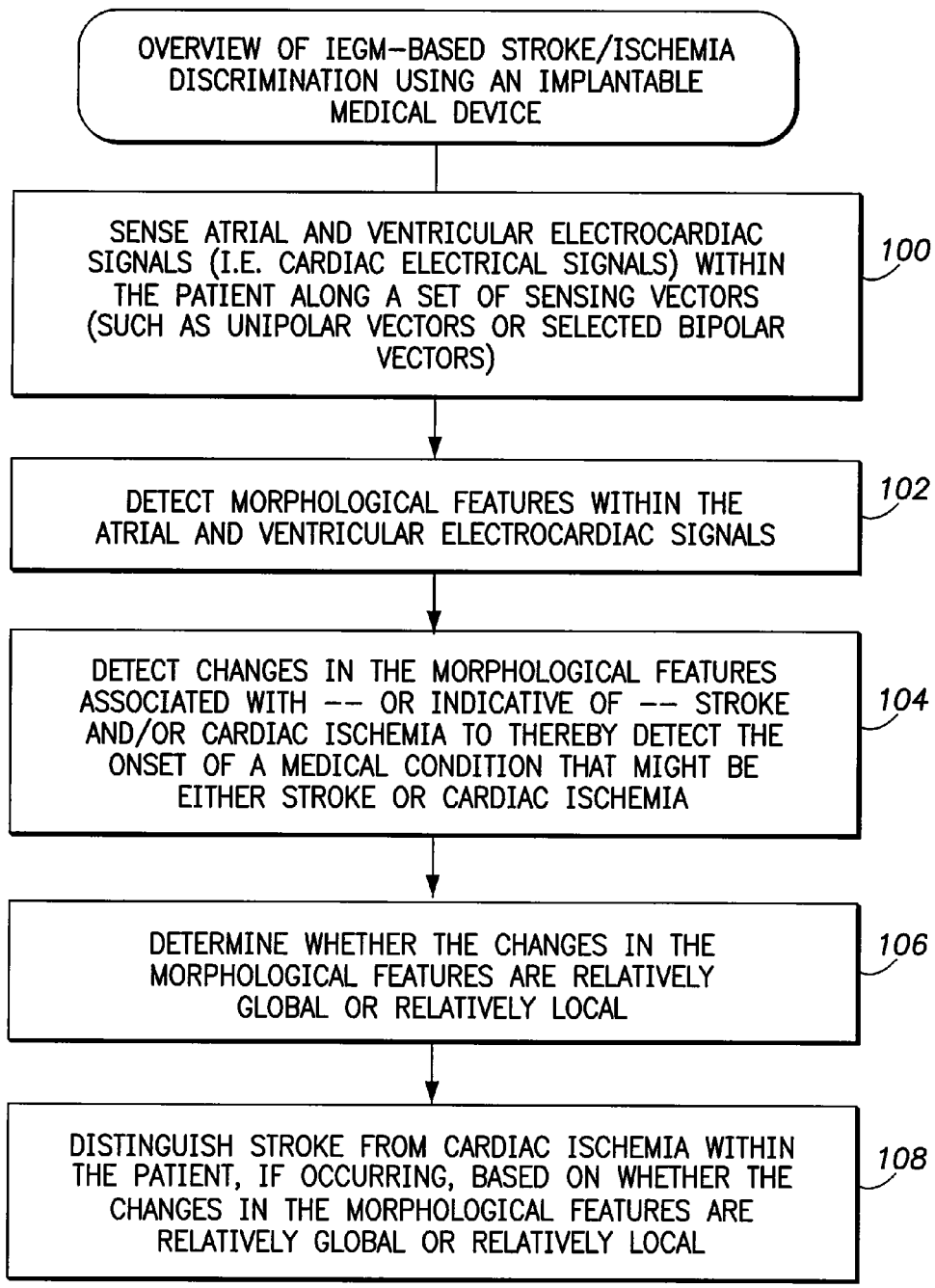
FIG. 2 provides an overview of the method for detecting and distinguishing stroke and cardiac ischemia for use by the system of FIG. 1, which exploits changes in selected morphological features of atrial and ventricular unipolar electrocardiac signals.

FIG. 2 summarizes the stroke/cardiac ischemia detection and discrimination procedure employed by the pacer/ICD of FIG. 1. Initially, at step 100, the pacer/ICD senses atrial and ventricular electrocardiac signals (i.e. cardiac electrical signals) within the patient along a set of sensing vectors such as along at least one atrial unipolar vector and along at least one ventricular unipolar vector. At step 102, the pacer/ICD detects morphological features within the atrial and ventricular electrocardiac signals such as PR intervals within the atrial signals and ST intervals, QT intervals and T-waves within the ventricular signals. These and other exemplary morphological features will be discussed in greater detail below. At step 104, the pacer/ICD detects changes in the morphological features that are associated with—or indicative of—stroke and/or cardiac ischemia. Examples include changes in the elevations of the PR and ST intervals, the durations of QT intervals and the shape of the T-waves. This, too, will be discussed in greater detail below. By detecting changes in the morphological features that are associated with—or indicative of—stroke and/or cardiac ischemia, the pacer/ICD thereby detects the onset of a medical condition that might be either stroke or cardiac ischemia and hence further discrimination is warranted.

Insofar as cardiac ischemia is concerned, note that changes within myocardial tissues affected by the ischemia can affect the electrocardiac signals produced during and after contraction, which can affect numerous features of the corresponding IEGM. Insofar as stroke is concerned, a cerebral stroke—whether ischemic or hemorrhagic—can also produce changes in the IEGM. These IEGM changes are likely due to extreme sympathetic neural stimulation associated with stroke, which in turn may be associated with raised intracranial pressures arising due to the stroke. Augmentation of intra-cardiac sympathetic nerve activity seems to occur, resulting, e.g., in IEGM repolarization changes. Nevertheless, regardless of the physiological mechanism by which the stroke causes changes in the IEGM, these changes (or trends therein) are typically detectable within an IEGM.

At step 106, the pacer/ICD determines whether the changes in the morphological features are relatively global or relatively local. A relatively global change is one that affects all (or most) of the signals more or less equally and, in particular, significantly affects both the atrial and ventricular IEGM signals. A relatively local change is one that affects one or only a few of the signals more significantly than others. For example, a significant change observed only in ventricular unipolar IEGM signals but not atrial unipolar IEGM signals is a relatively local change. Likewise, a significant change observed only in atrial unipolar IEGM signals but not in ventricular unipolar IEGM signals is a relatively local change. Note that, in some examples, bipolar signals may instead be used, particularly to assess local changes in the IEGM (since bipolar sensing vectors are well-suited to assess local IEGM changes.) At step 108, the pacer/ICD then distinguishes stroke from cardiac ischemia within the patient, if occurring, based on whether the changes in the morphological features are relatively global or relatively local. Global changes are deemed to be indicative of stroke. Local changes are deemed to be indicative of cardiac ischemia. As noted above, disruptions in blood supply to the brain caused by stroke may lead to alterations of cardiac autonomic tone, such as increased sympathetic nerve activity. Thus stroke may lead to neurally mediated changes in electrophysiological properties of the heart. See, for example, Taggart et al. "Heart-brain Interactions in Cardiac Arrhythmia" Heart 2011; 97: 698-708.) Thereafter, the pacer/ICD generates warning signals indicative of stroke or cardiac ischemia, delivers appropriate therapy, records diagnostics and/or performs other suitable responsive functions as will be discussed below.

Exemplary Unipolar IEGM-based Stroke/Ischemia Discrimination Techniques

Figures 1, 3:
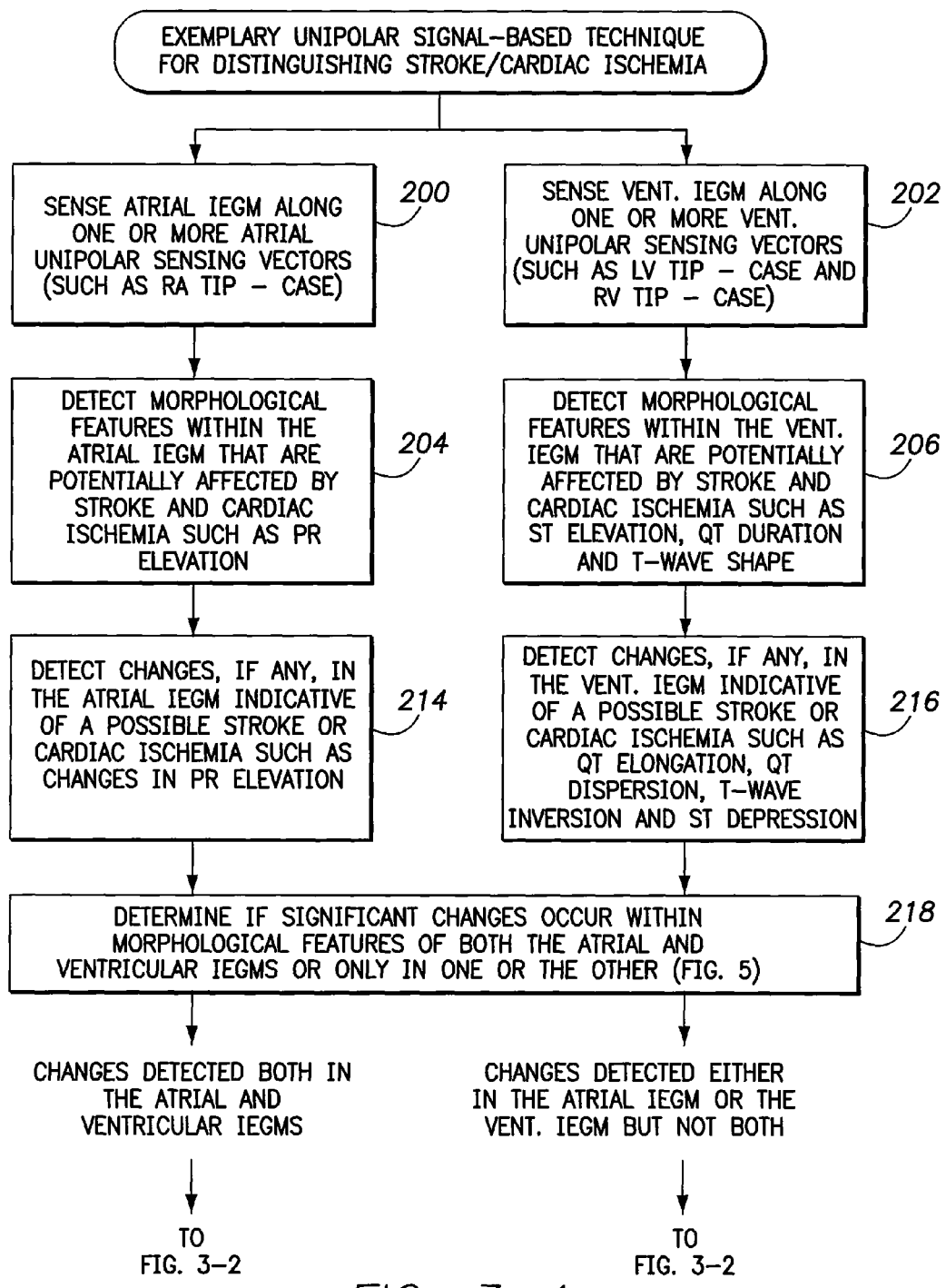
Figures 2, 3:
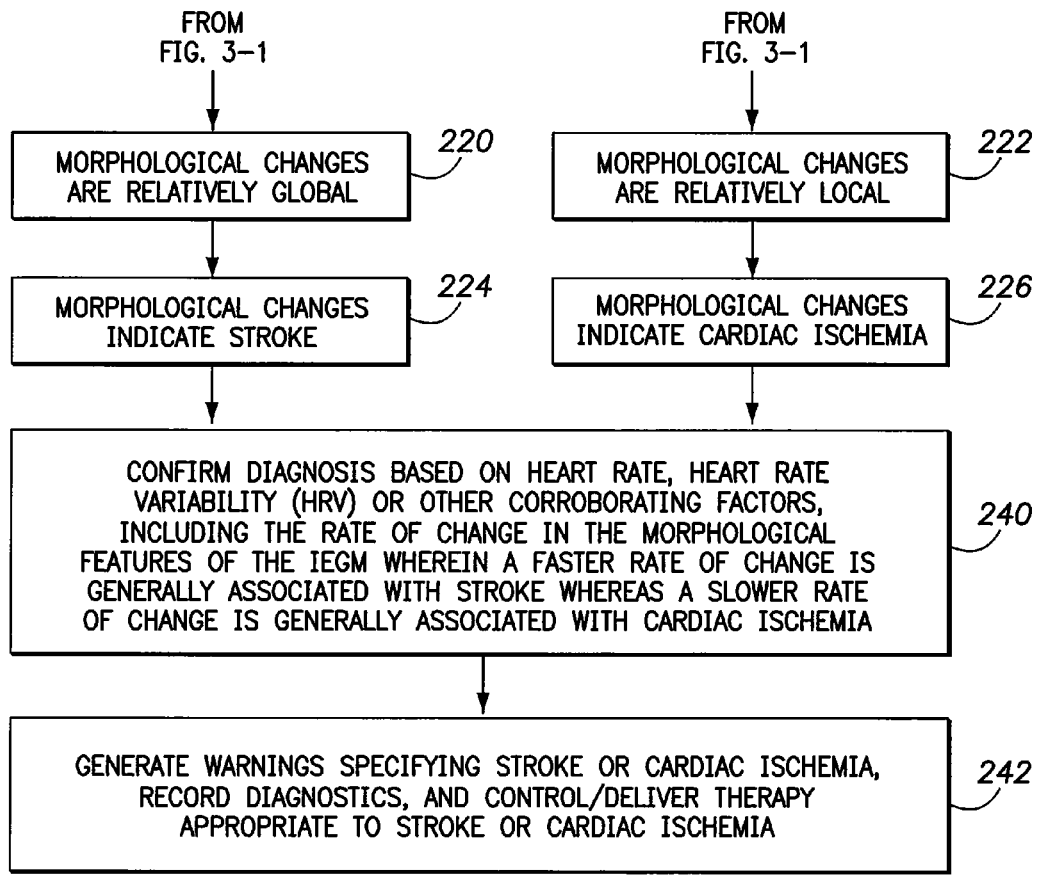

FIG. 3 illustrates an exemplary stroke/ischemia detection and discrimination technique that exploits morphological features of atrial and ventricular unipolar IEGM signals. The pacer/ICD further utilizes physiological and/or hemodynamic parameters to confirm or disconfirm the diagnosis. Initially, at step 200, the pacer/ICD senses atrial IEGM signals along one or more atrial unipolar sensing vectors (such as RA tip-case). Concurrently, at step 202, the pacer/ICD also senses ventricular IEGM signals along one or more ventricular unipolar sensing vectors (such as LV tip—case and RV tip—case). Table I provides a list of unipolar sensing vectors that are typically available and programmable within state-of-the-art pacemakers, ICDs and CRTs.

TABLE I

| Unipolar Electrode (used with "can" return electrode) | Pacemaker | ICD | CRT |
|---|---|---|---|
| RA tip | x | x | x |
| RA ring | x | x | x |
| RV tip | x | x | x |
| RV ring | x | x | x |
| RV coil | | x | x |
| SVC coil | | x | x |
| LV tip | | | x |
| LV ring1 | | | x |
| LV ring2 | | | x |
| LV ring3 | | | x |

In some examples, a single atrial unipolar vector is selected for use along with a single ventricular unipolar vector to detect and distinguish stroke and cardiac ischemia. In other examples, a greater number of unipolar vectors can be exploited. For example, the device might be programmed to combine RA tip and RA ring unipolar signals to obtain a single atrial unipolar IEGM for monitoring. Likewise, the device might be programmed to combine LV tip and RV tip unipolar signals to obtain a single ventricular unipolar IEGM. If the device is a CRT, it might be programmed to combine all four LV unipolar signals to obtain a single combined LV unipolar IEGM for monitoring. In still other examples, assuming a sufficient number of sensing channels are available within the device, the device might be programmed to separately track and analyze each of the available unipolar signals to provide further specificity to the location of a cardiac ischemia, assuming one is found to have occurred. For the purposes of FIG. 3, it will be assumed that one atrial unipolar IEGM and one ventricular unipolar IEGM are used, where the ventricular unipolar IEGM is derived from a combination of LV tip and RV tip unipolar signals.

At step 204, the pacer/ICD detects morphological features within the atrial IEGM that are potentially affected by stroke and cardiac ischemia such as PR elevation and ST elevation. Concurrently, at step 206, the pacer/ICD detects morphological features within the ventricular IEGM that are potentially affected by stroke and cardiac ischemia such as ST elevation, QT duration and T-wave shape. For ST elevation measurement techniques, see, e.g., U.S. patent application Ser. No. 12/016,166 of Boileau et al., filed Jan. 17, 2008, entitled "Systems and Methods for Distinguishing Cardiac Ischemia from Systemic Influences on IEGM Morphology using an Implantable Medical Device."

Figure 4:
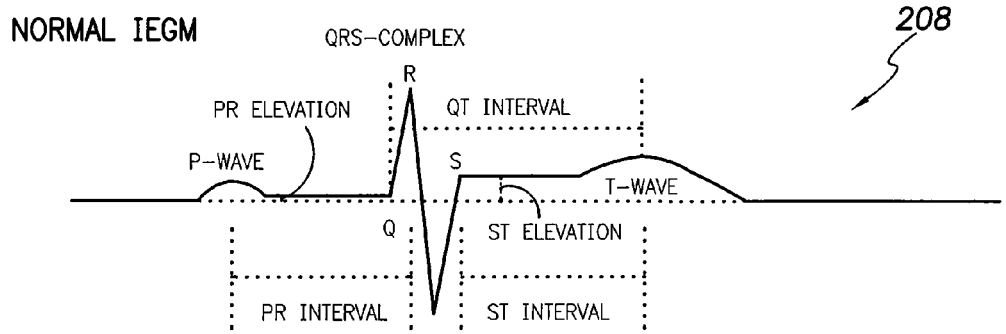
FIG. 4 provides graphs illustrating exemplary morphological parameters within an IEGM exploited by the technique of FIG. 3.
Figure 4:
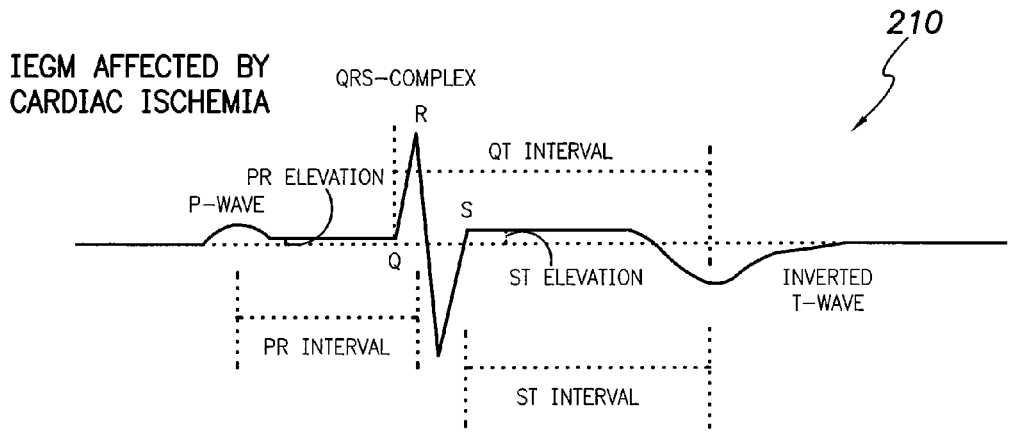
Figure 4:
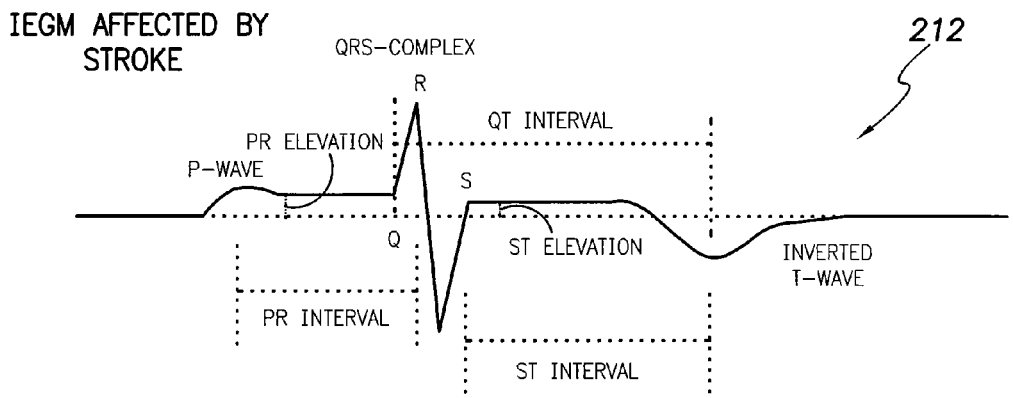

FIG. 4 illustrates exemplary morphological features of the IEGM that can be affected by both stroke and cardiac ischemia. A first stylized IEGM trace 208 corresponding to a single heartbeat illustrates a P-wave (i.e. atrial depolarization) followed by a QRS-complex (i.e. ventricular depolarization) followed by a T-wave (i.e. ventricular repolarization.) Note that this exemplary trace is a ventricular channel IEGM trace and so the P-wave shown therein is a "far field" event, which actually arises in the atria. In practice, the P-wave (and any morphological features associated with the P-wave) would preferably be detected within a separate atrial IEGM. Ventricular IEGMs are presented in FIG. 4 simply because this conveniently allows for both atrial and ventricular morphological features to be shown within the heartbeat traces.

Heartbeat trace 208 further illustrates the PR interval, which extends from the peak of the P-wave to the peak of the QRS-complex and also illustrates the PR elevation, which is the voltage difference (if any) between the flat portion of the PR interval and an isoelectric baseline. In this example, the PR elevation is positive but in other cases, it might instead be negative. Again, in practice, these atrial morphological features are preferably measured by the device within a separate atrial IEGM signal. Still further, heartbeat trace 208 illustrates the ST interval, which extends from the end of the QRS-complex to the peak of the T-wave and also illustrates the ST elevation, which is the voltage difference (if any) between the flat portion of the ST interval and the isoelectric baseline. As with the PR elevation, the ST elevation may be positive or negative. Trace 208 also illustrates the QT interval, which extends from the start of the QRS-complex to the peak of the T-wave (i.e. QTmax). The QT interval could instead be defined relative to the end of the T-wave (QTend) rather than its peak. The peak of the T-wave is typically chosen since it is more easily detected. Note also that both QTmax and QTend could be detected and separately tracked. Still further, the ST segment could instead be defined relative to the beginning of the T-wave. Insofar as the ST interval is concerned, it is the elevation of the interval that is of particular interest and hence the point used to define the end of the interval is somewhat arbitrary. Note also that any depression of the ST interval, as well as the direction of any ST change, is of interest and can be influenced by the location of an occlusion.

As second trace 210 shows how these parameters might be affected by cardiac ischemia. In this example, although the atrial morphology (e.g. PR elevation) has not changed significantly, the ventricular parameters are strongly affected. The ST elevation is depressed. The T-wave has become inverted and its peak delayed relative to the QRS-complex. As such, the QT interval is elongated. Given that the ventricular features have changed but the atrial features have not, the example of trace 210 illustrates the affect of a cardiac ischemia in the ventricles. A third trace 212 shows how the morphological features can be affected by stroke. In this example, in addition to changes to the ventricular parameters, the atrial PR elevation has also shifted upwardly. Given that both the atrial and ventricular features have changed significantly, the example of trace 212 illustrates the affect of stroke.

Figure 5:
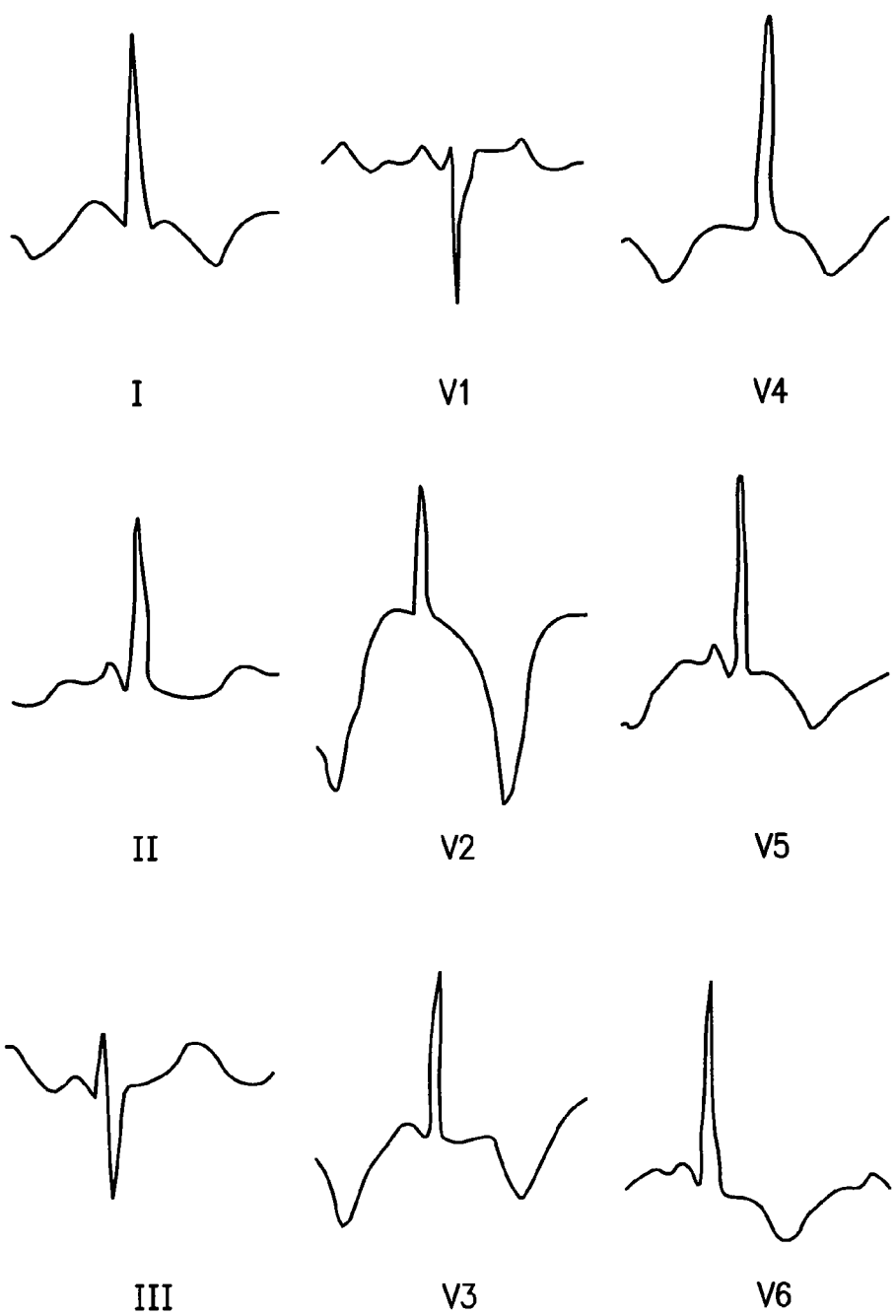
FIG. 5 illustrates the type of changes to cardiac signals that can be observed due to stroke.

FIG. 5 further illustrates the type of changes to cardiac signals that can be observed due to stroke. More specifically, a set of traces 213 provide stylized representations of surface electrocardiogram (EKG) signals observed in response to stroke. (See, Burch et al. "A New Electrocardiographic Pattern Observed in Cerebrovascular Accidents" Circulation 9:720, 1954.) As can be seen, significant changes in the T-wave are observed. Although these changes are shown within a surface EKG (for illustrative purposes), it should be understood that corresponding changes may be identified with an IEGM detected by an implantable device.

Returning to FIG. 3, at step 214, the pacer/ICD detects changes, if any, in the atrial IEGM indicative of a possible stroke or cardiac ischemia such as the aforementioned shift in PR elevation. Concurrently, at step 216, the pacer/ICD detects changes, if any, in the ventricular IEGM indicative of a possible stroke or cardiac ischemia such as QT elongation, QT dispersion, T-wave inversion and ST depression. QT dispersion refers to an increase in the variation in the QT interval from one heartbeat to the next, which can increase in response to stroke or cardiac ischemia. These are just some examples of parameters that might be affected by stroke and cardiac ischemia. Other morphological features of the IEGM can potentially be affected as well, such as notches within T-waves or the onset of prominent U-waves. U-waves are thought to represent electrical repolarization of the papillary muscles or Purkinje fibers. U-waves are not always present in the IEGM but can become prominent during a stroke and possibly also during cardiac ischemia. T-wave notches and U-waves are discussed in the Patent Applications of Park cited above (Application No. 2010/0198082 and Ser. No. 12/722,206.)

Still other electrocardiac parameters that potentially may be exploited include various duration-based parameters such as P-wave width, QRS-complex width and T-wave width; various slope-based parameters such as maximum P-wave slope, maximum QRS-complex slope and maximum T-wave slope; various amplitude-based parameters such as peak P-wave amplitude, peak QRS-complex amplitude and peak T-wave amplitude; as well as various interval-based parameters such as atrioventricular (AV) intervals.

At step 218, the pacer/ICD determines if significant changes occur within the morphological features of both the atrial and ventricular IEGMs or only in one or the other. Exemplary techniques for making this determination are described below with reference to FIG. 6. If significant changes detected both in the atrial and ventricular IEGMs, then at step 220 the pacer/ICD concludes that the morphological changes are "relatively global." Otherwise, if significant changes are detected either in the atrial IEGM or in the ventricular IEGM, but not both, then at step 222 the pacer/ICD concludes that the morphological changes are "relatively local." If relatively global, the pacer/ICD thereby concludes at step 224 that the morphological changes observed in the IEGMs are more likely indicative of stroke rather than cardiac ischemia. If relatively local, the pacer/ICD thereby concludes at step 226 that the morphological changes are more likely indicative of cardiac ischemia than stroke.

At step 240, the pacer/ICD then preferably attempts to confirm the diagnosis based on heart rate, HRV or other corroborating factors including the rate of change in the morphological features of the IEGM, wherein a faster rate of change is generally associated with stroke, whereas a slower rate of change is generally associated with cardiac ischemia. That is, for each morphological parameter of the IEGM of interest, the rate of change of the parameter can be assessed and compared against a corresponding predetermined rate threshold indicative of possible stroke vs. possible cardiac ischemia, where faster rates are typically associated with stroke as opposed to cardiac ischemia. In this regard, it is noted that stroke-related cardiac signal changes have dynamicity over time. (See, e.g., Jensen et al. "Prevalence of Electrocardiographic ST-T Changes During Acute Ischemic Stroke in Patients Without Known Ischemic Heart Disease." Int J. Cardiol., Volume 128, Issue 1, 1 Aug. 2008, Pages 137-138) The dynamic variability of the monitored features (include ST level, T-wave inversion, QT elongation, QT dispersion and HRV) can therefore provide additional specificity when compared with cardiac ischemia.

Exemplary techniques for confirming or corroborating the discrimination of stroke and cardiac ischemia based on other signals or parameters are discussed below with reference to FIG. 7. At step 242, the pacer/ICD generates warnings specifying stroke or cardiac ischemia, records suitable diagnostics and/or controls the delivery of therapy appropriate to stroke or cardiac ischemia. Given the possible severity of a stroke, a prompt and urgent warning is preferably generated. In one particular example, the bedside monitor issues a loud alarm to notify family members or caregivers of the stroke. The warning signals can also be relayed to the patient's primary care physician or directly to emergency personnel.

Insofar as therapy is concerned, a variety of responses might be triggered in response to stroke, depending upon the capabilities of the implantable system. For example, suitable neurostimulation might be delivered via the spinal cord, baro-receptors or sympathetic nerves, again depending upon the capabilities of the device. Spinal cord stimulation via an implantable lead is discussed, e.g., in U.S. Pat. No. 7,099,718 to Thacker, et al. Baro-receptor stimulation to control blood pressure is discussed in U.S. Pat. No. 6,050,952 to Hakki, et al. Techniques for stimulating sympathetic nerves are discussed in U.S. Pat. No. 6,937,896 to Kroll, entitled, "Sympathetic Nerve Stimulator and/or Pacemaker."

As to possible medications, tPA tissue plasminogen activator or like compounds can be automatically delivered to help restore blood flow to the brain immediately following a stroke. (Note that tPA tissue plasminogen activator is a thrombolytic agent, i.e. a compound for breaking down clots). After the stroke event has ended, anticoagulants can be delivered to prevent subsequent stokes, particularly in patients known to have atrial fibrillation or a heart-valve disorder. Suitable versions of these or other compounds may be identified for dispensing via an implantable drug dispensing unit, drug infusion unit and/or drug pump under the control of the pacer/ICD. See, e.g., U.S. Pat. No. 7,235,530 to Blair, et al., entitled "Kallikrein Inhibitors and Anti-Thrombolytic Agents and Uses Thereof," which discusses compounds suitable for delivery via a medication infusion pump.

These and other responses to stroke are discussed in the above-cited application of Bharmi et al. (Ser. No. 12/558,385) and in the applications of Park (2010/0198082 and Ser. No. 12/722,206.) If the device is equipped with a separate stroke detection system, it might be desirable in some implementations to confirm the detection of stroke using the alternative system before therapy is delivered. See, for example, the stroke detection systems set forth in Bharmi et al. (Ser. No. 12/558,385.) A questionnaire, such as the type described by Park (2010/0198082), might also be employed before therapy is delivered, if a caregiver or family member is available to answer the questions. Still further, since other medical conditions can have systemic (i.e. global) affects on electrocardiac signals, such as hypoglycemia or hyperglycemia, additional electrocardiac parameters can be examined and analyzed to provide further diagnostic specificity. See, for example, the techniques described within the Fard et al. patent cited above (U.S. Pat. No. 7,756,572) and within the Boileau et al. patent application (Ser. No. 12/016,166). See, also, the various techniques described in the aforementioned U.S. Patents and U.S. patent applications entitled "System and Method for Distinguishing among Cardiac Ischemia, Hypoglycemia and Hyperglycemia using an Implantable Medical Device."

Pacing therapy may be adjusted in response to cardiac ischemia. Adjustments to pacing therapy in response to cardiac ischemia may involve, for example, reduction of a base pacing rate so as to prevent a relatively high programmed base rate from exacerbating the ischemia. Anti-thrombolytics or other medications can be delivered using an implanted drug pump, if one is provided. Routine experimentation may be employed to identify medications for treatment of cardiac ischemia that are safe and effective for use in connection with an implantable drug pump.

Neurostimulation can be provided in response to ischemia. See, for example, U.S. Pat. Nos. 7,869,869 and 7,813,805 of Farazi, both entitled "Subcardiac Threshold Vagal Nerve Stimulation."

Figure 6:
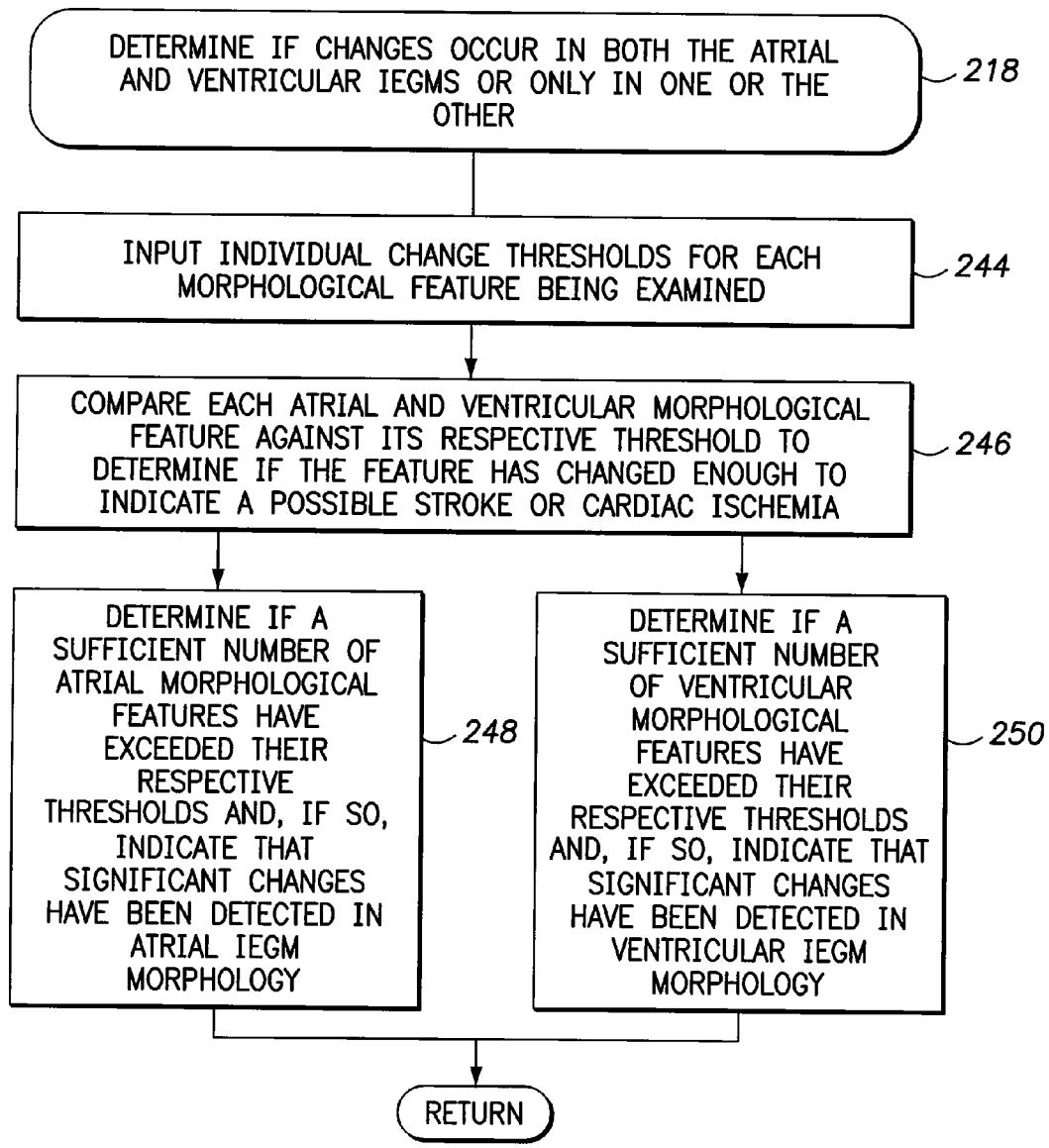
FIG. 6 illustrates an exemplary technique for use with the method of FIG. 3, wherein separate thresholds are used to assess the magnitude of changes to the morphological parameters observed in various unipolar signals.

Turning now to FIG. 6, exemplary techniques for use at step 218 of FIG. 3 will be described to determine if significant changes have occurred both in the atrial and ventricular IEGMs or only in one or the other. At step 244, the pacer/ICD inputs individual predetermined change thresholds for each morphological feature being examined. That is, one threshold is input for ST segment depression, another for QT interval elongation, etc. Still further, different thresholds can be established for use with different signal vectors. That is, the threshold applied to ST shift observed in an LV IEGM might be different from the thresholds applied to ST shift observed in an RV IEGM. At step 246, the pacer/ICD compares each atrial and ventricular morphological feature against its respective threshold to determine if the feature has changed enough to indicate a possible stroke or cardiac ischemia. The thresholds can be specified in terms of percentage changes such that if a given parameter changes by more that the specified percentage, the change is deemed to be significant. The thresholds may be initially set based on clinical studies of populations of patients known to have suffered strokes.

At step 248, the pacer/ICD determines if a sufficient number of atrial morphological features have exceeded their respective thresholds and, if so, the device concludes that significant changes have been detected in atrial IEGM morphology. Concurrently, the pacer/ICD determines if a sufficient number of ventricular morphological features have exceeded their respective thresholds and, if so, the device concludes that significant changes have been detected in the ventricles. In some cases, only a single morphological parameter might be examined for a given IEGM channel. For example, for the atrial IEGM, only PR elevation might be monitored. If so, then it is sufficient that the one parameter exceeds its threshold. If multiple morphological parameters are examined such as within the ventricular IEGM, the device might specify that some minimum number of the parameters need to exceed their respective threshold. Alternatively, a single "score" can be generated based on multiple parameters for comparison against a single threshold. Also, note that if a greater number of IEGM signals are examined, i.e. more than just one atrial and one ventricular IEGM, the analysis of FIG. 6 can be applied to each separate IEGM to determine which particular signal vectors exhibit significant change.

Figure 7:
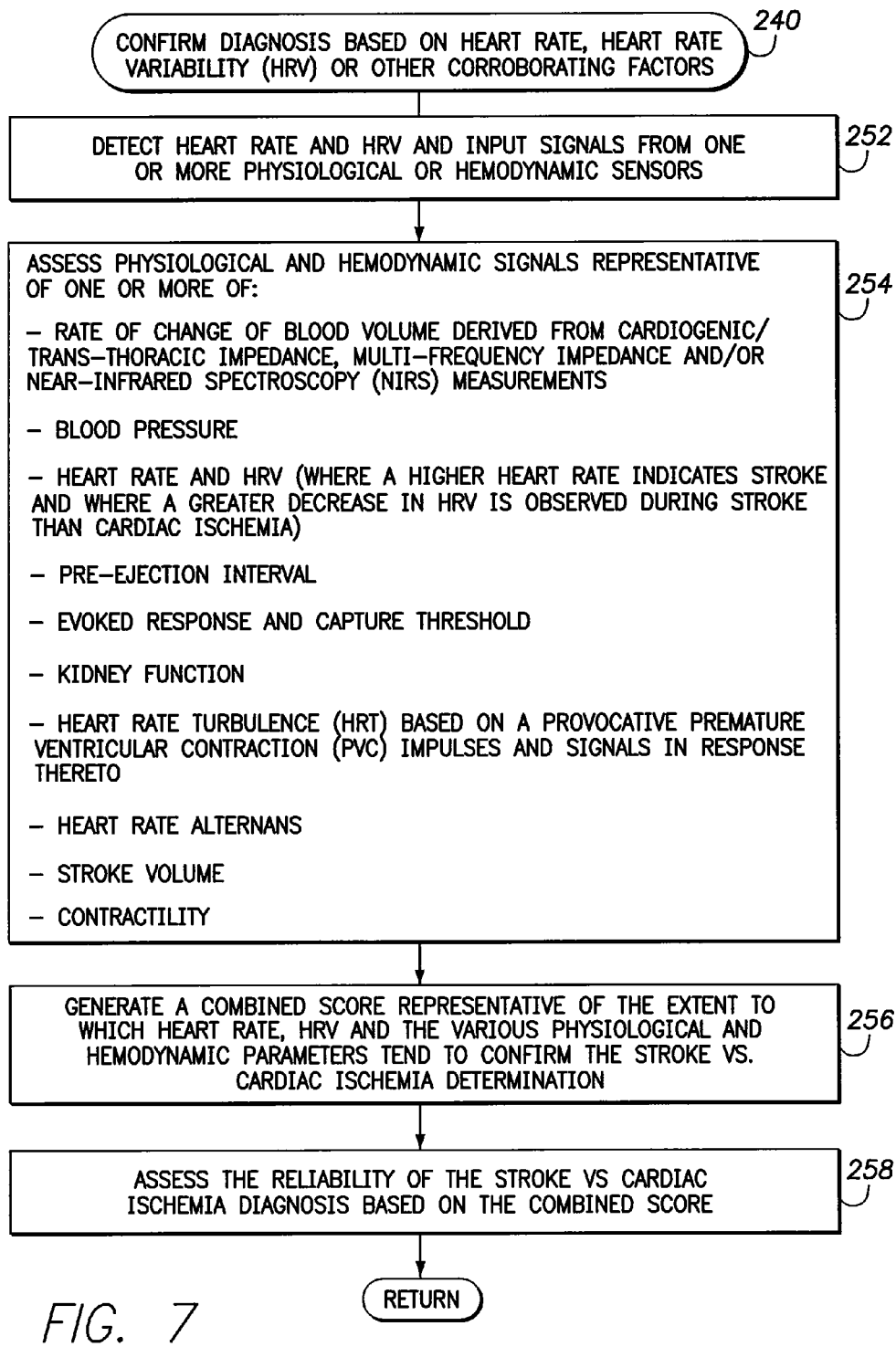
FIG. 7 illustrates an exemplary technique for use with the method of FIG. 3, wherein various physiological and hemodynamic parameters are used to corroborate the determination of stroke vs. cardiac ischemia.

FIG. 7 illustrates exemplary techniques for use at step 240 of FIG. 3 to confirm diagnosis based on heart rate, HRV or other corroborating factors. At step 252, the pacer/ICD detects heart rate and HRV and input signals from one or more physiological or hemodynamic sensors, such as sensors mounted on the leads or mounted on or within the pacer/ICD. Various sensors are discussed in: U.S. patent application Ser. No. 11/856,443, of Zhao, filed Sep. 17, 2007, entitled "MEMS-Based Left Atrial Pressure Sensor for use with an Implantable Medical Device" and in U.S. patent application Ser. No. 11/623,663, filed Jan. 16, 2007, of Zou et al., entitled "Sensor/Lead Systems for use with Implantable Medical Devices."

At step 254, the pacer/ICD then assess signals representative of one or more of: the rate of change (if any) in blood volume derived from cardiogenic/trans-thoracic impedance, multi-frequency impedance and/or near-infrared spectroscopy (NIRS) measurements; blood pressure; cardiac rhythm including heart rate and HRV, where a lower heart rate indicates cardiac ischemia and an higher heart rate indicates stroke; pre-ejection interval; evoked response; capture threshold; kidney function; heart rate turbulence based on a provocative premature ventricular contraction (PVC) impulses and signals in response thereto; heart rate alternans; stroke volume; and contractility. These parameters are assessed to determine if they are consistent with the determination made at steps 224 and 226 of stroke vs. ischemia.

Insofar as blood volume is concerned, the pacer/ICD can exploit various impedance or NIRS measurements to assess particular blood volume parameters such as LV volume or LA volume. In general, blood volume can change during either a stroke or a local cardiac ischemia (depending on the severity of the ischemia.) In this regard, the blood volume in the chambers are likely to change in response to sympathetic surge in response to stroke to a larger degree compared to the changes in response to ischemia (i.e. the ischemic region might get akinetic and hence might affect the contractility and hence the blood volume to a small degree depending on the segment affected.) Hence, the rate at which blood volume changes will likely be much faster in stroke. Accordingly, it is desirable to assess the rate of change of blood volume and to associate a faster change in blood volume with stroke and a slower change in blood volume with cardiac ischemia. Techniques for assessing various blood volume parameters based on impedance are described, for example, in U.S. patent application Ser. No. 12/853,130 of Gutfinger et al., filed Aug. 9, 2010, entitled "Near Field-Based Systems and Methods for Assessing Impedance and Admittance for use with an Implantable Medical Device" and in U.S. patent application Ser. No. 13/007,424 also of Gutfinger et al. filed Jan. 14, 2011, entitled "Systems and Methods for Exploiting Near-Field Impedance and Admittance for use with Implantable Medical Devices."

Insofar as blood pressure and cardiac rhythm are concerned, certain changes in these parameters are characteristic of stroke. For example, a sudden increase in blood pressure and heart rate may arise due to autonomic reaction in response to an ischemic stroke. Conversely, in response to cardiac ischemia, a gradual decline in pressure may be observed due to weakening myocardial performance. Blood pressure may be detected using any suitable blood pressure sensor or sensing technique. Particularly effective techniques for detecting blood pressure values are discussed in U.S. Pat. No. 7,654,964 to Kroll et al., entitled, "System and Method for Detecting Arterial Blood Pressure based on Aortic Electrical Resistance using an Implantable Medical Device."

Cardiac rhythm—including heart rate and HRV—can be assessed based on the various IEGM signals. Particularly effective techniques for measuring and quantifying HRV are described, for example, in U.S. patent application Ser. No. 12/558,385 of Bharmi et al., cited above. HRV is a measure of the variation in heart rate over time. Briefly, in one example described therein, HRV is assessed based on an analysis of R-R intervals, including various frequency components thereof. HRV can be reduced by both stroke and cardiac ischemia. However, as noted above, reductions in HRV may be more pronounced from stroke than when cardiac ischemia occurs and hence HRV can be used to discriminate stroke from cardiac ischemia, at least within some patients. One possible reason for this difference is that the efferent neural pathways involved in heart rate control are affected by stroke, but not necessarily from a site of cardiac ischemia. For a discussion of the effects of stroke on HRV see, for example, Tokgözoglu at al. "Effects of Stroke Localization on Cardiac Autonomic Balance and Sudden Death" Stroke 1999, 30, 1307-1311.

Insofar as the pre-ejection interval is concerned, this interval—also called the pre-ejection period (PEP)—is the time from the ventricular depolarization corresponding to the QRS complex and the onset of ventricular ejection, which can be measured using the IEGM signal and a blood flow sensor, impedance sensor, or a ventricular volume detector, etc. See, for example, U.S. Pat. No. 4,719,921 to Chirife. The pre-ejection interval tends to become longer in response to cardiac ischemia but becomes shorter in response to stroke.

Insofar as the evoked response is concerned, the magnitude of an evoked response, which is an electrical signal triggered in response to pacing pulses, is more likely to change in response to a cardiac ischemia than a stroke. The evoked response may be measured within the IEGM. See, for example, U.S. Pat. No. 6,473,647 to Bradley, entitled "Implantable Cardiac Stimulation Device For and Method of Monitoring Progression or Regression of Heart Disease by Monitoring Evoked Response Features" and U.S. Pat. No. 6,711,439, also to Bradley, et al., entitled "Evoked Response Variability as an Indicator of Autonomic Tone and Surrogate for Patient Condition."

Capture thresholds, which are representative of the amount of stimulation energy required to depolarize the myocardium in the vicinity of a stimulation electrode, can increase due to cardiac ischemia. Hence, if IEGM morphology changes and, simultaneously, the capture threshold increase at a single electrode within the LV, then cardiac ischemia is indicated rather than stroke. Changes in the capture threshold can be detected based on detection of loss of capture or by performing capture threshold assessment procedures.

Insofar as kidney function is concerned, IEGM morphology changes can be associated with renal failure, including renal failure occurring in the absence of a stroke. However, any IEGM changes due to renal failure should be a relatively slow process that can be distinguished from IEGM changes due to either stroke or ischemia, which would be faster. Hence, the device can distinguish IEGM changes due to renal failure from those due to stroke or ischemia. Techniques for detecting renal failure are discussed in U.S. Pat. Nos. 7,529, 580 and 7,400,920, entitled "Detection of Renal Failure by Cardiac Implantable Medical Device."

Insofar as heart rate turbulence (HRT) is concerned, HRT is generally regarded as a physiological response of the sinus node of the heart to premature ventricular contractions (PVCs.) HRT can be assessed based on provocative PVC impulses and signals in response thereto. HRT is expected to be affected by either cardiac ischemia or stroke. In this regard, the intrinsic cardiac nervous system might be affected by the sympathetic surge or changes in the extrinsic nervous system (depending on region of brain affected.) This intrinsic nervous system influence on turbulence might be present in both ischemia or stroke. Nevertheless, when combined with other IEGM changes specific to stroke, HRT information can be helpful, at least to corroborate stroke detection. Exemplary techniques for measuring HRT are also described in U.S. patent application Ser. No. 12/558,385 of Bharmi et al.

Heart rate alternans pertain to alternations in the contraction of the heart. For example, T-wave alternans (TWA) pertain to a periodic beat-to-beat variation in the amplitude or shape of the T-wave in the IEGM (typically, high/low amplitudes occurring at odd/even beats.) TWA, which can be detected within the IEGM, is discussed, e.g., in U.S. Pat. No. 7,245,968 to Farazi, et al., entitled "Implantable Cardiac Device Providing Rapid Pacing T wave Alternan Pattern Detection and Method." See, also, U.S. Pat. Nos. 7,756,571; 7,738,956; 7,697,978; 7,620,448; and 7,599,733 and U.S. Published Patent Application No. 2009/0318822, all assigned to Pacesetter Inc. Alternans are often observed in response to cardiac ischemia but not stroke.

Stroke volume can decrease in response to cardiac ischemia but is not expected to decrease significantly in response to stroke. If stroke volume is found to have decreased, then the change is deemed to be consistent with cardiac ischemia rather than stroke. Stroke volume sensors are described in U.S. Pat. No. 6,961,615 to Kroll, et al., entitled "System and Method for Evaluating Risk of Mortality due to Congestive Heart Failure using Physiologic Sensors." Impedance-based techniques for detecting stroke volume are discussed in U.S. Pat. No. 7,139,609 to Min, et al., "System and Method for Monitoring Cardiac Function via Cardiac Sounds using an Implantable Cardiac Stimulation Device."

Cardiac contractility can also decrease in response to cardiac ischemia but is not expected to decrease significantly in response to stroke. Hence, if cardiac contractility is found to have decreased, this change is deemed to be consistent with cardiac ischemia rather than stroke. Techniques for detecting contractility are discussed in, e.g., U.S. Pat. No. 6,788,970 to Park, et al., entitled "System and Method for Treating Vasovagal Syncope using Cardiac Pacing." As described therein, an implanted device can determine a patient's current contractility based on, for example, ventricular gradient, impedance, heart sounds, PEP, etc. For example, contractility may be measured using pressure waves. See, e.g., U.S. Pat. No. 6,208,900 to Ecker et al. and U.S. Pat. No. 4,485,813 to Anderson et al. Heart sound waves can also be used to determine contractility and other related parameters (e.g., stroke volume, blood pressure and dP/dt), as disclosed in U.S. Pat. No. 6,044,299 to Nilsson.

IEGM signals may also be basis for determining contractility, e.g., using the IEGM to derive a "ventricular gradient" and QT interval. "Ventricular gradient," also sometimes referred to as "paced depolarization integral," is the integral of the paced R-wave (or P-wave) signal and is also believed to correlate to contraction force. See, for example, U.S. Pat. No. 4,759,366 to Callaghan.

Impedance measurements of blood in the heart can also been employed to derive contractility of the myocardium and stroke volume. See, U.S. Pat. No. 4,884,576 to Alt and U.S. Pat. No. 4,535,774 to Olsen. Also, the rate of change in impedance (dZ/dt) has been shown to correspond to contractility. See, for example, U.S. Pat. No. 4,733,667 to Olive et al. and U.S. Pat. No. 5,800,467 to Park et al. Particularly effective "tri-phasic" impedance pulses for use in detecting impedance are discussed in U.S. patent application Ser. No. 11/558,194, of Panescu et al., filed Nov. 9, 2006, entitled "Closed-Loop Adaptive Adjustment of Pacing Therapy Based on Cardiogenic Impedance Signals Detected by an Implantable Medical Device." In some examples, surrogates for myocardial contractility are derived from cardiac pressure signals or PPG signals. See, for example, techniques described in published U.S. Patent Application No. 2010/0234906 of Koh, entitled "System and Method for Controlling Rate-Adaptive Pacing based on a Cardiac Force-Frequency Relation detected by an Implantable Medical Device."

At step 256, the pacer/ICD generates a combined score representative of the extent to which a combination of heart rate, HRV and the various physiological and hemodynamic signals and parameters tend to confirm the determination of stroke vs. cardiac ischemia originally made at steps 224 and 226 of FIG. 3. Particularly effective techniques for combining different parameters into a single metric value for evaluation are set forth in U.S. Pat. No. 7,207,947 to Koh et al., entitled "System and Method for Detecting Circadian States Using an Implantable Medical Device."

At step 258, the pacer/ICD assesses the reliability of the stroke vs. cardiac ischemia diagnosis based on the combined score. This may be achieved, for example, by comparing the combined score against a predetermined threshold. If the combined score exceeds the threshold, the previous diagnosis is confirmed. Otherwise, the diagnosis is disconfirmed. If confirmed, the device responds to the detected medical condition by generating warnings, delivering therapy, etc, as already described. If disconfirmed, the device may repeat the analysis of FIGS. 3 and 6 based on newly detected parameters and signals. Note that the particular value of the threshold used at step 258 will depend on the particular parameters used to generate the combined score and may vary from patient to patient, subject to clinician programming.

Exemplary Identifying the Location of a Cardiac Ischemia

Figure 8:
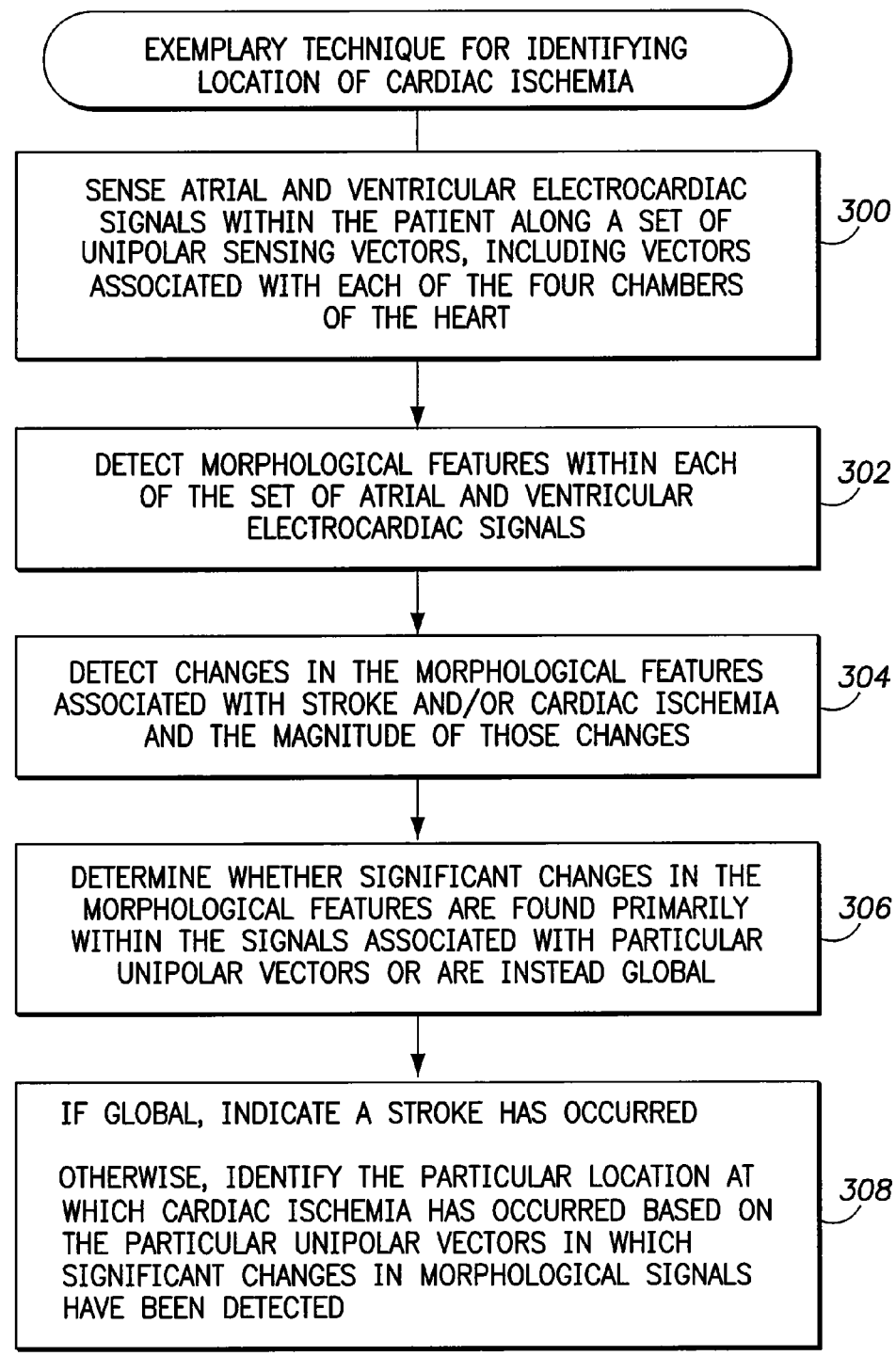
FIG. 8 provides an overview of a method for distinguishing stroke and cardiac ischemia for use by the system of FIG. 1, which also serves to identify the location of a cardiac ischemia if one is occurring.

FIG. 8 summarizes techniques for identifying the location within the heart of a cardiac ischemia (in addition to distinguishing stroke from cardiac ischemia.) These techniques may be used in conjunction with the techniques already described. Many of the steps are the same or similar to those of FIG. 2 and will not be described again in detail. At step 300, the implantable device senses atrial and ventricular electrocardiac signals within the patient along a set of unipolar sensing vectors including vectors associated with each of the chambers of the heart. That is, the device preferably senses electrocardiac signals along at least one RA unipolar vector, at least one LA unipolar vector, at least one LV unipolar vector, and at least one RV unipolar vector. If the device is equipped with a multi-pole LV/CD lead such as the Quartet™ lead of St. Jude Medical, the device preferably senses unipolar vectors using each of the four electrodes of the multipole lead.

At step 302, the device detects morphological features within each of the set of atrial and ventricular electrocardiac signals, such as the aforementioned PR intervals, ST intervals, QT intervals, etc. The particular features to be detected will depend upon the particular unipolar vector, with atrial parameters being detected within atrial vectors and ventricular parameters being detected within ventricular vectors. At step 304, the device detects changes in the morphological features associated with stroke and/or cardiac ischemia and the magnitude of those changes, as already described. At step 306, the device then determines whether significant changes in the morphological features are found primarily within the signals associated with particular unipolar vectors, such as just the atrial vectors or just the ventricular vectors, or whether the changes are instead global.

At step 308, if global, the device indicates that a stroke has occurred, as discussed above. Otherwise, the device identifies the particular location at which cardiac ischemia has occurred based on the particular unipolar vectors in which significant changes in morphological signals have been detected. For example, if significant changes are observed only in the unipolar signals of LA vectors, then an LA cardiac ischemia is indicated. If significant changes are observed only in the unipolar signals of LV vectors, then an LV cardiac ischemia is indicated. Assuming the device is equipped with a multipole lead, the device can further specify the location within the LA that the ischemia occurred. The determination of which unipolar vectors exhibit significant changes can be based on the magnitude of the changes. For example, if all of the LV vectors show significant changes in the morphological features, but one of the vectors exhibits changes of much greater magnitude than the others, then the device concludes that the vector exhibiting the largest change corresponds to the location of the cardiac ischemia.

Hence, FIG. 8 illustrates techniques for identifying the location of a cardiac ischemia. As can be appreciated, these techniques can be applied with varying degrees of precision. In some example, the device might only distinguish between atrial and ventricular ischemias. In other examples, the device distinguishes between RA, LA, RV, and LV ischemias. In still other examples, as explained, the device can further specify the location the ischemia within a particular chamber, assuming the device is equipped with suitable multipolar leads.

Exemplary Techniques for Detecting Cardiac Ischemia During Stroke

Figure 9:
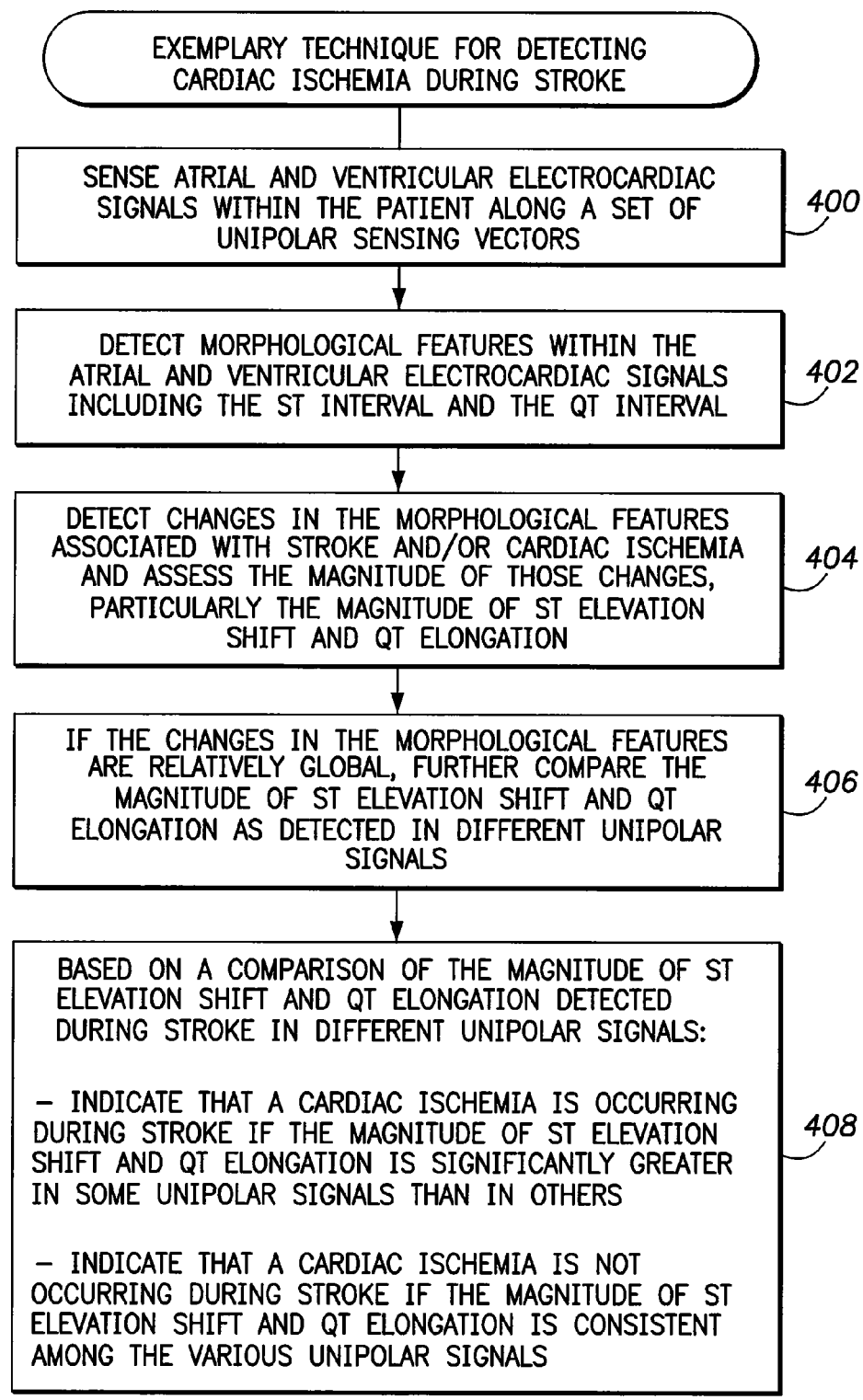
FIG. 9 provides an overview of a method for distinguishing stroke and cardiac ischemia for use by the system of FIG. 1, which also serves to detect a cardiac ischemia occurring during stroke.

FIG. 9 summarizes techniques for detecting a possible cardiac ischemia occurring during a stroke. These techniques may be used in conjunction with the techniques already described. Again, many of the steps are the same or similar to those already described and will not be described again in detail. At step 400, the implantable device senses atrial and ventricular electrocardiac signals within the patient along a set of unipolar sensing vectors including vectors associated with each of the chambers of the heart. At step 402, the device detects morphological features within each of the set of atrial and ventricular electrocardiac signals. At step 404, the device detects changes in the morphological features associated with stroke and/or cardiac ischemia and the magnitude of those changes, particularly the magnitude of any changes in ST elevation and QT duration. At step 406, if the changes in the morphological features are relatively global (i.e. significant changes are observed in all of the unipolar signals), the device further compares the magnitude of ST elevation shift and QT elongation as detected in different unipolar signals. That is, even in circumstances where global changes are observed (indicating a stroke), the device further compares the signals to detect a possible cardiac ischemia contemporaneous with the stroke.

At step 408, based on a comparison of the magnitude of ST elevation shift and QT elongation detected during stroke in different unipolar signals, the device: indicates that a cardiac ischemia is occurring during stroke if the magnitude of ST elevation shift and QT elongation is significantly greater in some unipolar signals than in others; and indicates that a cardiac ischemia is not occurring during stroke if the magnitude of ST elevation shift and QT elongation is consistent among the various unipolar signals. Suitable warning signals can then be generated indicating "stroke only" or "stroke plus cardiac ischemia." The therapy to be delivered by the device may vary depending upon whether cardiac ischemia is occurring along with stroke.

Thus, exemplary techniques have been described for detecting and distinguishing stroke and cardiac ischemia. The above-described techniques can be implemented with a variety of implantable medical devices. For the sake of completeness, a pacer/ICD/CRT implementation will now be described in detail where a multipole LV lead is employed.

Exemplary Pacer/ICD/CRT

Figure 11:
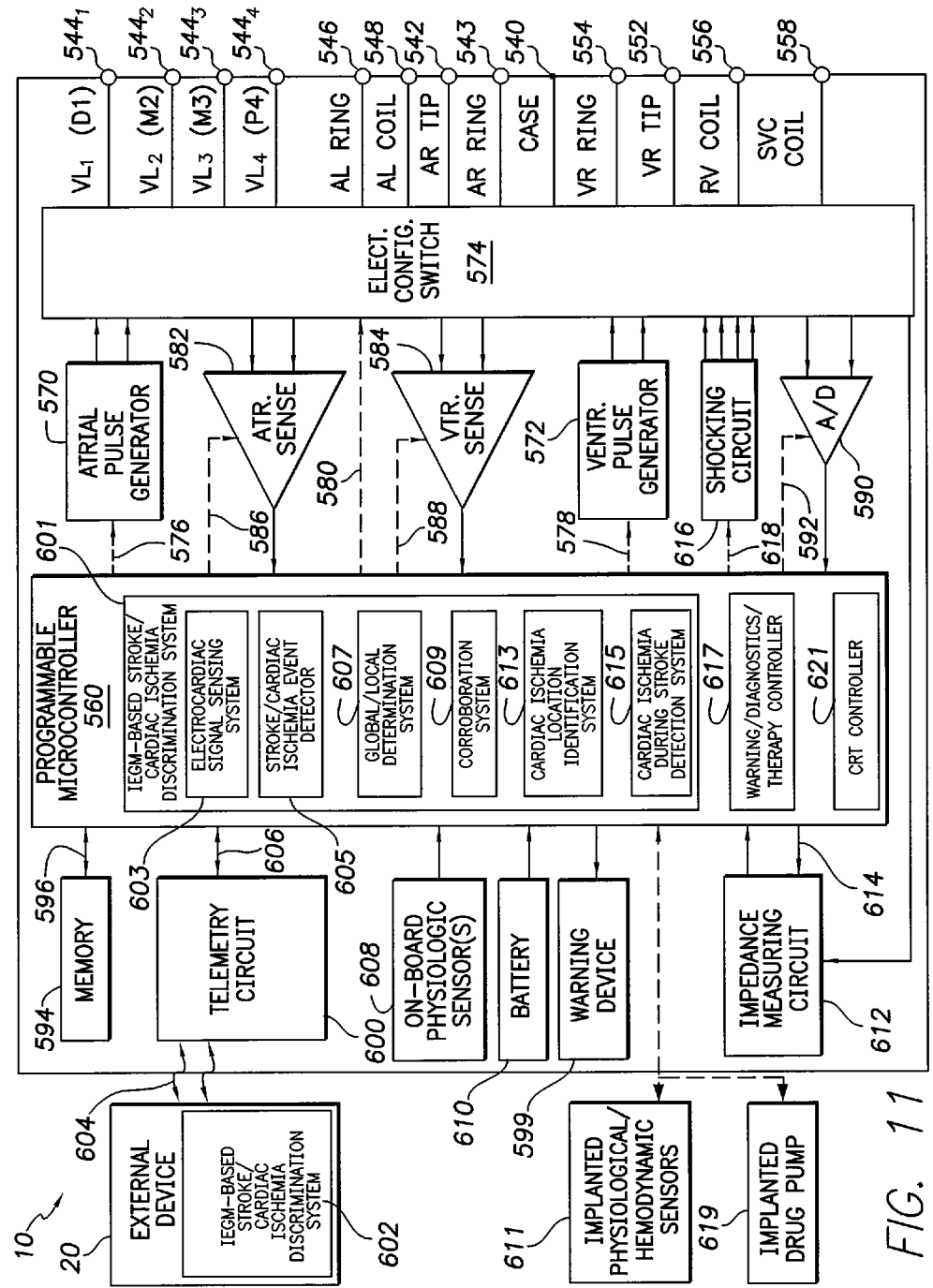
FIG. 11 is a functional block diagram of the pacer/ICD of FIG. 10, illustrating basic device circuit elements that provide cardioversion, defibrillation and/or pacing stimulation in four chambers of the heart, and particularly illustrating components within the device for detecting and distinguishing stroke from cardiac ischemia based on unipolar atrial and ventricular IEGM signals.

With reference to FIGS. 10 and 11, a description of an exemplary pacer/ICD will now be provided. FIG. 10 provides a simplified block diagram of the device, which is a dual-chamber stimulation device capable of treating both fast and slow arrhythmias with stimulation therapy, including cardioversion, defibrillation, and pacing stimulation, and also capable of discriminating stroke and cardiac ischemia, as discussed above, and for controlling functions in response thereto. To provide other atrial chamber pacing stimulation and sensing, device 10 is shown in electrical communication with a heart 512 by way of a right atrial lead 18 having an atrial tip electrode 522 and an atrial ring electrode 523 implanted in the atrial appendage. Device 10 is also in electrical communication with the heart by way of a right ventricular lead 14 having, in this embodiment, a ventricular tip electrode 532, a right ventricular ring electrode 534, a right ventricular (RV) coil electrode 536, and a superior vena cava (SVC) coil electrode 538. Typically, the right ventricular lead 14 is transvenously inserted into the heart so as to place the RV coil electrode 536 in the right ventricular apex, and the SVC coil electrode 538 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, device 10 is coupled to a multi-pole LV lead 16 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 16 is designed to receive atrial and ventricular cardiac signals and to deliver left ventricular pacing therapy using a set of four left ventricular electrodes $526_1$ (D1), $526_2$ (M2), $526_3$ (M3), and $526_4$ (P4) (thereby providing a quad-pole lead), left atrial pacing therapy using at least a left atrial ring electrode 527, and shocking therapy using at least a left atrial coil electrode 528 implanted on or near the left atrium. In other examples, more or fewer LV electrodes are provided. Although only three leads are shown in FIG. 10, it should be understood that additional leads (with one or more pacing, sensing and/or shocking electrodes) might be used and/or additional electrodes might be provided on the leads already shown, such as additional electrodes on the RV lead.

A simplified block diagram of internal components of device 10 is shown in FIG. 11. While a particular device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 540 for device 10, shown schematically in FIG. 11, is often referred to as the "can," "case" or "case electrode" and may be programmably selected to act as the return electrode for all "unipolar" modes. The housing 540 may further be used as a return electrode alone or in combination with one or more of the coil electrodes, 528, 536 and 538, for shocking purposes. The housing 540 further includes a connector (not shown) having a plurality of terminals, 542, 543, $544_1$-$544_4$, 546, 548, 552, 554, 556 and 558 (shown schematically and, for convenience, the names of the electrodes to which they are connected are shown next to the terminals). As such, to achieve right atrial sensing and pacing, the connector includes at least a right atrial tip terminal ($A_R$ TIP) 542 adapted for connection to the atrial tip electrode 522 and a right atrial ring ($A_R$ RING) electrode 543 adapted for connection to right atrial ring electrode 523. To achieve left chamber sensing, pacing and shocking, the connector includes a left ventricular tip terminal ($VL_1$ TIP) $544_1$ and additional LV electrode terminals $544_2$-$544_4$ for the other LV electrodes of the quadra-pole LV lead.

The connector also includes a left atrial ring terminal ($A_L$ RING) 546 and a left atrial shocking terminal ($A_L$ COIL) 548, which are adapted for connection to the left atrial ring electrode 527 and the left atrial coil electrode 528, respectively. To support right chamber sensing, pacing and shocking, the connector further includes a right ventricular tip terminal ($V_R$ TIP) 552, a right ventricular ring terminal ($V_R$ RING) 554, a right ventricular shocking terminal ($V_R$ COIL) 556, and an SVC shocking terminal (SVC COIL) 558, which are adapted for connection to the right ventricular tip electrode 532, right ventricular ring electrode 534, the $V_R$ coil electrode 536, and the SVC coil electrode 538, respectively.

At the core of pacer/ICD 10 is a programmable microcontroller 560, which controls the various modes of stimulation therapy. As is well known in the art, the microcontroller 560 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 560 includes the ability to process or monitor input signals (data) as controlled by a program code stored in a designated block of memory. The details of the design and operation of the microcontroller 560 are not critical to the invention. Rather, any suitable microcontroller 560 may be used that carries out the functions described herein. The use of microprocessor-based control circuits for performing timing and data analysis functions are well known in the art.

As shown in FIG. 11, an atrial pulse generator 570 and a ventricular pulse generator 572 generate pacing stimulation pulses for delivery by the right atrial lead 18, the right ventricular lead 14, and/or the LV/CS lead 16 via an electrode configuration switch 574. It is understood that in order to provide stimulation therapy in each of the four chambers of the heart, the atrial and ventricular pulse generators, 570 and 572, may include dedicated, independent pulse generators, multiplexed pulse generators or shared pulse generators. The pulse generators, 570 and 572, are controlled by the microcontroller 560 via appropriate control signals, 576 and 578, respectively, to trigger or inhibit the stimulation pulses.

The microcontroller 560 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 574 includes a plurality of switches for connecting the desired electrodes to the appropriate I/O circuits, thereby providing complete electrode programmability. Accordingly, the switch 574, in response to a control signal 580 from the microcontroller 560, determines the polarity of the stimulation pulses (e.g., unipolar, bipolar, combipolar, etc.) by selectively closing the appropriate combination of switches (not shown) as is known in the art.

Atrial sensing circuits 582 and ventricular sensing circuits 584 may also be selectively coupled to the right atrial lead 18, LV/CS lead 16, and the right ventricular lead 14, through the switch 574 for detecting the presence of cardiac activity in each of the four chambers of the heart. Accordingly, the atrial (ATR. SENSE) and ventricular (VTR. SENSE) sensing circuits, 582 and 584, may include dedicated sense amplifiers, multiplexed amplifiers or shared amplifiers. The switch 574 determines the "sensing polarity" of the cardiac signal by selectively closing the appropriate switches, as is also known in the art. In this way, the clinician may program the sensing polarity independent of the stimulation polarity. Each sensing circuit, 582 and 584, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 582 and 584, are connected to the microcontroller 560 which, in turn, are able to trigger or inhibit the atrial and ventricular pulse generators, 570 and 572, respectively, in a demand fashion in response to the absence or presence of cardiac activity in the appropriate chambers of the heart.

For arrhythmia detection, pacer/ICD 10 utilizes the atrial and ventricular sensing circuits, 582 and 584, to sense cardiac signals to determine whether a rhythm is physiologic or pathologic. As used in this section, "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 560 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 590. The data acquisition system 590 is configured to acquire intracardiac electrogram signals, convert the raw analog data into a digital signal, and store the digital signals for later processing and/or telemetric transmission to an external device 16. The data acquisition system 590 is coupled to the right atrial lead 18, the LV/CS lead 16, and the right ventricular lead 14 through the switch 574 to sample cardiac signals across any pair of desired electrodes. The microcontroller 560 is further coupled to a memory 594 by a suitable data/address bus 596, wherein the programmable operating parameters used by the microcontroller 560 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 594 through a telemetry circuit 600 in telemetric communication with the external device 20, such as a programmer, transtelephonic transceiver or a diagnostic system analyzer. The telemetry circuit 600 is activated by the microcontroller by a control signal 606. The telemetry circuit 600 advantageously allows intracardiac electrograms and status information relating to the operation of pacer/ICD 10 (as contained in the microcontroller 560 or memory 594) to be sent to the external device 16 through an established communication link 604. The external device 20 may alternatively be a bedside monitor or PAM, as already discussed.

Pacer/ICD 10 further includes an on-board accelerometer or other physiologic sensor or sensors 608, sometimes referred to as a "rate-responsive" sensor because it is typically used to adjust pacing stimulation rate according to the exercise state of the patient. However, physiological or hemodynamic sensor(s) 608 can be equipped to sense any of a variety of cardiomechanical parameters, such as heart sounds, systemic pressure, etc. As can be appreciated, at least some these sensors may be mounted outside of the housing of the device and, in many cases, will be mounted to the leads of the device. Moreover, the physiological sensor 608 may further be used to detect changes in cardiac output, changes in the physiological condition of the heart, or diurnal changes in activity (e.g., detecting sleep and wake states) and to detect arousal from sleep. Accordingly, the microcontroller 560 responds by adjusting the various pacing parameters (such as rate, AV delay, V-V delay, etc.) at which the atrial and ventricular pulse generators, 570 and 572, generate stimulation pulses. While shown as being included within pacer/ICD 10, it is to be understood that physiologic/hemodynamic sensors may also be external to pacer/ICD 10, yet still be implanted within or carried by the patient. This is shown by way of physiological/hemodynamic sensor(s) 611. A common type of internal rate responsive sensor is an activity sensor incorporating an accelerometer or a piezoelectric crystal and/or a 3D-accelerometer capable of determining the posture within a given patient, which is mounted within the housing 540 of pacer/ICD 10. Other types of physiologic sensors are also known, for example, sensors that sense the oxygen content of blood, respiration rate and/or minute ventilation, pH of blood, ventricular gradient, etc., The pacer/ICD additionally includes a battery 610, which provides operating power to all of the circuits shown in FIG. 11. The battery 610 may vary depending on the capabilities of pacer/ICD 10. If the system only provides low voltage therapy, a lithium iodine or lithium copper fluoride cell typically may be utilized. For pacer/ICD 10, which employs shocking therapy, the battery 610 should be capable of operating at low current drains for long periods, and then be capable of providing high-current pulses (for capacitor charging) when the patient requires a shock pulse. The battery 610 should also have a predictable discharge characteristic so that elective replacement time can be detected. Accordingly, appropriate batteries are employed.

As further shown in FIG. 11, pacer/ICD 10 is shown as having an impedance measuring circuit 612, which is enabled by the microcontroller 560 via a control signal 614. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; measuring intracardiac impedance; and detecting the opening of heart valves, etc. The impedance measuring circuit 612 is advantageously coupled to the switch 674 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 560 further controls a shocking circuit 616 by way of a control signal 618. The shocking circuit 616 generates shocking pulses of low (up to 0.5 joules), moderate (0.5-10 joules) or high energy (11 to 40 joules or more), as controlled by the microcontroller 560. Such shocking pulses are applied to the heart of the patient through at least two shocking electrodes, and as shown in this embodiment, selected from the left atrial coil electrode 528, the RV coil electrode 536, and/or the SVC coil electrode 538. The housing 540 may act as an active electrode in combination with the RV electrode 536, or as part of a split electrical vector using the SVC coil electrode 538 or the left atrial coil electrode 528 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 6-40 joules), delivered asynchronously (since R-waves may be too disorganized), and pertaining exclusively to the treatment of fibrillation. Accordingly, the microcontroller 560 is capable of controlling the synchronous or asynchronous delivery of the shocking pulses.

Insofar as stroke/cardiac ischemia discrimination is concerned, the microcontroller includes an on-board stroke/cardiac ischemia discrimination system 601 operative to distinguish stroke from cardiac ischemia within the patient. System 601 includes an electrocardiac signal sensing system 603 operative to sense atrial and ventricular electrocardiac signals within the patient along a plurality of sensing vectors, which might be unipolar or bipolar depending upon the particular implementation and the selected vector. Sensing system 603 operates in conjunction with the atrial and ventricular sense amplifiers 582 and 584. A stroke/cardiac ischemia event detector 605 is operative to detect morphological features within the signals and further operative to detect changes in the morphological features associated with stroke and cardiac ischemia. A global/local determination system 607 is operative to determine whether the changes in the morphological features are relatively global or relatively local.

Using these components, the stroke/cardiac ischemia discrimination system distinguishes stroke from cardiac ischemia within the patient, if occurring, based on whether the changes in the morphological features are relatively global or relatively local, as discussed above in connection with FIGS. 2-6. A corroboration system 609 is operative to corroborate the discrimination of stroke from cardiac ischemia as discussed above in connection with FIG. 7 based on one or more of physiological signals and hemodynamic signals received from on-board sensor(s) 608 or implanted sensor(s) 611, which are external to the device by implanted within the patient. Still further, a cardiac ischemia location identification system 613 is operative identify the location within the heart of a cardiac ischemia, as discussed above in connection with FIG. 8. A cardiac ischemia during stroke detection system 615 is operative to detect a cardiac ischemia occurring during stroke, as discussed above in connection with FIG. 9. A warning/diagnostics/therapy controller 617 is provided to control the generation of warning signals, the recordation of diagnostics and the delivery of therapy, including any medicinal therapies delivered via an implanted drug pump 619, assuming one is provided. CRT may be controlled by a CRT controller 621.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

Additionally or alternatively, the aforementioned functions may be controlled or performed by an external system based on IEGM signals and other signals transmitted from the device. This is illustrated by way of an IEGM-based stroke/cardiac ischemia discrimination system 602 installed within the external device 20. The use of on-board components within device 10 is preferred since on-board components permit the device to promptly detect and respond to stroke and cardiac ischemia. Nevertheless, the provision of stroke/cardiac ischemia discrimination components within an external device may be advantageous, particularly for use with pacer/ICD/CRT devices not equipped with on-board stroke/ischemia discrimination components.

Still further, though examples herein exploit IEGM signals, at least some of the techniques can instead exploit subcutaneous electrocardiograms (ECGs) detected using subcutaneous (SubQ) devices. For a discussion of SubQ devices, see U.S. patent application Ser. No. 12/722,206 of Park, cited above.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable medical device for implant within a patient, the method comprising:
   sensing atrial and ventricular electrocardiac signals within the patient along a plurality of sensing vectors and detecting morphological features within the signals;
   detecting changes in the morphological features associated with both cerebral stroke and cardiac ischemia;
   determining whether the changes in the morphological features are relatively global or relatively local; and
   distinguishing cerebral stroke from cardiac ischemia within the patient, in response to the determining, based on whether the changes in the morphological features are relatively global or relatively local.

2. The method of claim 1 wherein detecting morphological features within the atrial and ventricular signals includes detecting one or more of: PR intervals; ST intervals; QT intervals; and T-waves.

3. The method of claim 2 wherein detecting changes in the morphological features associated with both cerebral stroke and cardiac ischemia includes detecting one or more of: PR elevation shift; ST depression; QT elongation; QT dispersion; and T-wave inversion.

4. The method of claim 1 wherein sensing atrial and ventricular electrocardiac signals within the patient along a plurality of sensing vectors comprises:
   sensing at least one atrial unipolar electrocardiac signal along at least one atrial unipolar sensing vector; and
   sensing at least one ventricular unipolar electrocardiac signal along at least one ventricular unipolar sensing vector.

5. The method of claim 4 wherein determining whether the changes are relatively global or relatively local comprises determining whether significant changes in the morphological features are present in both the atrial and ventricular electrocardiac signals.

6. The method of claim 1 further including identifying a location within the heart of a cardiac ischemia, if occurring.

7. The method of claim 1 wherein detecting changes in the morphological features of the electrocardiac signals includes detecting relative magnitudes of the changes along different sensing vectors.

8. The method of claim 7 further including detecting an indication of cardiac ischemia occurring during cerebral stroke based on comparison of the relative magnitudes of the changes in the morphological features along different sensing vectors.

9. The method of claim 8 wherein detecting an indication of cardiac ischemia occurring during stroke is based on the relative magnitude of changes in one or more of ST intervals and QT intervals along different sensing vectors.

10. The method of claim 8 wherein detecting an indication of cardiac ischemia occurring during cerebral stroke based on the magnitude of the changes in the morphological parameters is based on a comparison of changes detected within parameters detected within a subset of a plurality of electrocardiac signals as compared to all of said plurality of electrocardiac signals.

11. The method of claim 1 wherein distinguishing cerebral stroke from cardiac ischemia includes setting separate detection thresholds for each of a plurality of morphological parameters derived from different atrial and ventricular sensing vectors.

12. The method of claim 1 wherein distinguishing cerebral stroke from cardiac ischemia includes assessing a rate of change in the morphological features and associating a faster rate of change with cerebral stroke as opposed to cardiac ischemia.

13. The method of claim 1 wherein sensing atrial and ventricular electrocardiac signals within the patient along a plurality of sensing vectors comprises:
   sensing at least one bipolar electrocardiac signal along at least one bipolar sensing vector and detecting morphological features within the bipolar signal; and
   wherein determining whether the changes in the morphological features are relatively global or relatively local is based at least in part on the features derived from the bipolar signal.

14. The method of claim 1 further including controlling at least one device function in response to distinguishing cerebral stroke from cardiac ischemia within the patient.

15. The method of claim 14 wherein controlling at least one device function includes controlling one or more of: delivery of therapy, generation of warning signals and recordation of diagnostic information.

* * * * *